(12) United States Patent
Ryals et al.

(10) Patent No.: US 12,226,164 B2
(45) Date of Patent: Feb. 18, 2025

(54) SYSTEMS AND METHODS FOR PLANNING AND ASSISTING ORTHOPAEDIC SURGICAL PROCEDURES

(71) Applicant: DEPUY IRELAND UNLIMITED COMPANY, Ringaskiddy (IE)

(72) Inventors: Adam Ryals, Fuquay Varina, NC (US); Daniel Girardeau-Montaut, Grenoble (FR)

(73) Assignee: DEPUY IRELAND UNLIMITED COMPANY, Ringaskiddy (IE)

(*) Notice: Subject to any disclaimer, the term of this patent is extended or adjusted under 35 U.S.C. 154(b) by 230 days.

(21) Appl. No.: 18/091,486

(22) Filed: Dec. 30, 2022

(65) Prior Publication Data
US 2024/0216064 A1    Jul. 4, 2024

(51) Int. Cl.
A61B 34/10    (2016.01)
A61F 2/46     (2006.01)

(52) U.S. Cl.
CPC .............. *A61B 34/10* (2016.02); *A61F 2/461* (2013.01); *A61B 2034/107* (2016.02); *A61F 2002/4633* (2013.01)

(58) Field of Classification Search
CPC ... A61B 34/10; A61B 2034/107; A61F 2/461; A61F 2002/4633
See application file for complete search history.

(56) References Cited

U.S. PATENT DOCUMENTS 6,205,411 B1    3/2001  DiGioia, III et al.
8,010,180 B2    8/2011  Quaid et al.
(Continued)

FOREIGN PATENT DOCUMENTS

WO    2017106294 A2    6/2017
WO    2021170591 A1    9/2021
WO    2024008923 A1    1/2024

OTHER PUBLICATIONS

Doan, Jan. 2022, pp. 795-801.*
(Continued)

*Primary Examiner* — Michael I Ezewoko
(74) *Attorney, Agent, or Firm* — Barnes & Thornburg LLP

(57) ABSTRACT

Systems and methods for planning and assisting orthopaedic surgical procedures include a computer system and a robotic surgical device. The computer system receives multiple surgeon preferences, including target values and boundary values for surgical parameters of the orthopaedic surgical procedure. A surgeon uses the computer system to perform bony registration and leg-alignment registration for anatomy of a patient. The computer system determines a surgical plan for the orthopaedic surgical procedure based on the surgeon preferences, the bony registration, and the leg-alignment registration. The surgical plan includes planned values associated with the surgical parameters that are within the boundary values of the surgeon preferences. Determining the surgical plan may include automatically adjusting tibial coronal alignment, femoral coronal alignment, femoral flexion, femoral rotation, distal femoral resection height, proximal tibial resection height, and/or distal femoral resection height. The computer system may control the robotic surgical device according to the surgical plan.

18 Claims, 21 Drawing Sheets

(56) References Cited

U.S. PATENT DOCUMENTS

| | | | |
|---|---|---|---|
| 8,771,365 B2* | 7/2014 | Bojarski | A61F 2/3886 606/86 R |
| 8,926,706 B2* | 1/2015 | Bojarski | A61B 17/155 623/20.35 |
| 9,020,788 B2* | 4/2015 | Lang | A61F 2/30942 703/6 |
| 9,101,394 B2 | 8/2015 | Arata et al. | |
| 9,364,291 B2 | 6/2016 | Bellettre et al. | |
| 9,387,079 B2* | 7/2016 | Bojarski | A61F 2/30942 |
| 9,603,711 B2* | 3/2017 | Bojarski | A61B 17/155 |
| 9,665,686 B2 | 5/2017 | Van Vorhis et al. | |
| 9,826,981 B2* | 11/2017 | Schoenefeld | A61B 17/1764 |
| 9,827,051 B2 | 11/2017 | Arata et al. | |
| 9,913,692 B2 | 3/2018 | Arata et al. | |
| 9,916,421 B2 | 3/2018 | Van Vorhis et al. | |
| 10,064,685 B2 | 9/2018 | Bellettre et al. | |
| 10,813,574 B2 | 10/2020 | Fleig et al. | |
| 11,033,300 B2* | 6/2021 | Pavlovskaia | G16H 30/40 |
| 11,147,627 B2* | 10/2021 | Gangwar | G06T 7/73 |
| 11,158,415 B2* | 10/2021 | Daley | A61B 5/0082 |
| 11,376,072 B2 | 7/2022 | Bellettre et al. | |
| 11,744,643 B2* | 9/2023 | Rossetto | A61B 34/10 606/130 |
| 11,759,216 B2* | 9/2023 | Metcalfe | A61B 34/10 606/87 |
| 11,819,282 B2* | 11/2023 | Pavlovskaia | A61B 17/1703 |
| 11,847,755 B2* | 12/2023 | Park | B33Y 80/00 |
| 11,890,058 B2* | 2/2024 | Metcalfe | A61B 34/10 |
| 11,948,674 B2* | 4/2024 | Daley | A61B 34/30 |
| 2005/0251148 A1 | 11/2005 | Friedrich et al. | |
| 2007/0219561 A1 | 9/2007 | Lavallee et al. | |
| 2008/0269596 A1* | 10/2008 | Revie | A61B 90/39 705/28 |
| 2010/0076563 A1 | 3/2010 | Otto et al. | |
| 2010/0153081 A1 | 6/2010 | Bellettre et al. | |
| 2012/0041446 A1* | 2/2012 | Wong | A61F 2/30756 606/86 R |
| 2012/0165820 A1* | 6/2012 | De Smedt | A61B 17/175 29/428 |
| 2016/0228193 A1 | 8/2016 | Moctezuma de La Barrera et al. | |
| 2017/0065350 A1 | 3/2017 | Dossett et al. | |
| 2017/0265944 A1 | 9/2017 | Shupe et al. | |
| 2018/0132949 A1* | 5/2018 | Merette | G06T 11/60 |
| 2018/0233222 A1* | 8/2018 | Daley | G16H 50/50 |
| 2018/0360544 A1 | 12/2018 | Vanheule et al. | |
| 2020/0345421 A1 | 11/2020 | White et al. | |
| 2022/0008207 A1 | 1/2022 | Heldreth et al. | |
| 2022/0031473 A1* | 2/2022 | Carter | A61B 34/10 |
| 2022/0084652 A1* | 3/2022 | Daley | A61B 17/17 |
| 2022/0183757 A1* | 6/2022 | Caldera | A61B 90/39 |
| 2022/0183767 A1 | 6/2022 | Otto et al. | |
| 2022/0183774 A1 | 6/2022 | Merette et al. | |
| 2023/0080908 A1 | 3/2023 | Ali et al. | |
| 2023/0149090 A1 | 5/2023 | Angibaud et al. | |
| 2024/0008924 A1 | 1/2024 | Dressler et al. | |
| 2024/0008925 A1 | 1/2024 | Dressler et al. | |
| 2024/0216066 A1 | 7/2024 | Rock et al. | |
| 2024/0245460 A1* | 7/2024 | Utz | A61F 2/4657 |
| 2024/0282427 A1* | 8/2024 | Daley | A61B 34/32 |

OTHER PUBLICATIONS

Khamaisy, Elsevier, 2016, pp. 501-505.*
Miyasaka, 2017, Elsevier, pp. 47-52.*
Suero, Elsevier, 2013, pp. 268-271.*
Jacinto, 2018, Elsevier, pp. 167-177.*
Gibbons et al., "Development of a Statistical Shape-Function Model of the Implanted Knee for Real-Time Prediction of Joint Mechanics," Journal of Biomechanics, vol. 88, 2019, pp. 55-63.
Lambrechts et al., "Artificial Intelligence Based Patient-Specific Preoperative Planning Algorithm for Total Knee Arthroplasty," Frontiers in Robotics and AI, vol. 9, Mar. 8, 2022, 11 pages.
Brainlab AG, "Knee3 Surgical Technique," 2015, 58 pages.
Depuy Synthes, Velys Robotic-Assisted Solution for Total Knee, User Guide, Version 1.6, Rev. J, 2022, 217 pages.
Depuy Synthes, Velys Robotic-Assisted Solution for Total Knee, User Guide, Version 1.5, Rev. F, 2021, 214 pages.
International Search Report and Written Opinion for related International Application No. PCT/EP2023/085817, Mar. 18, 2024, 16 pages.

* cited by examiner

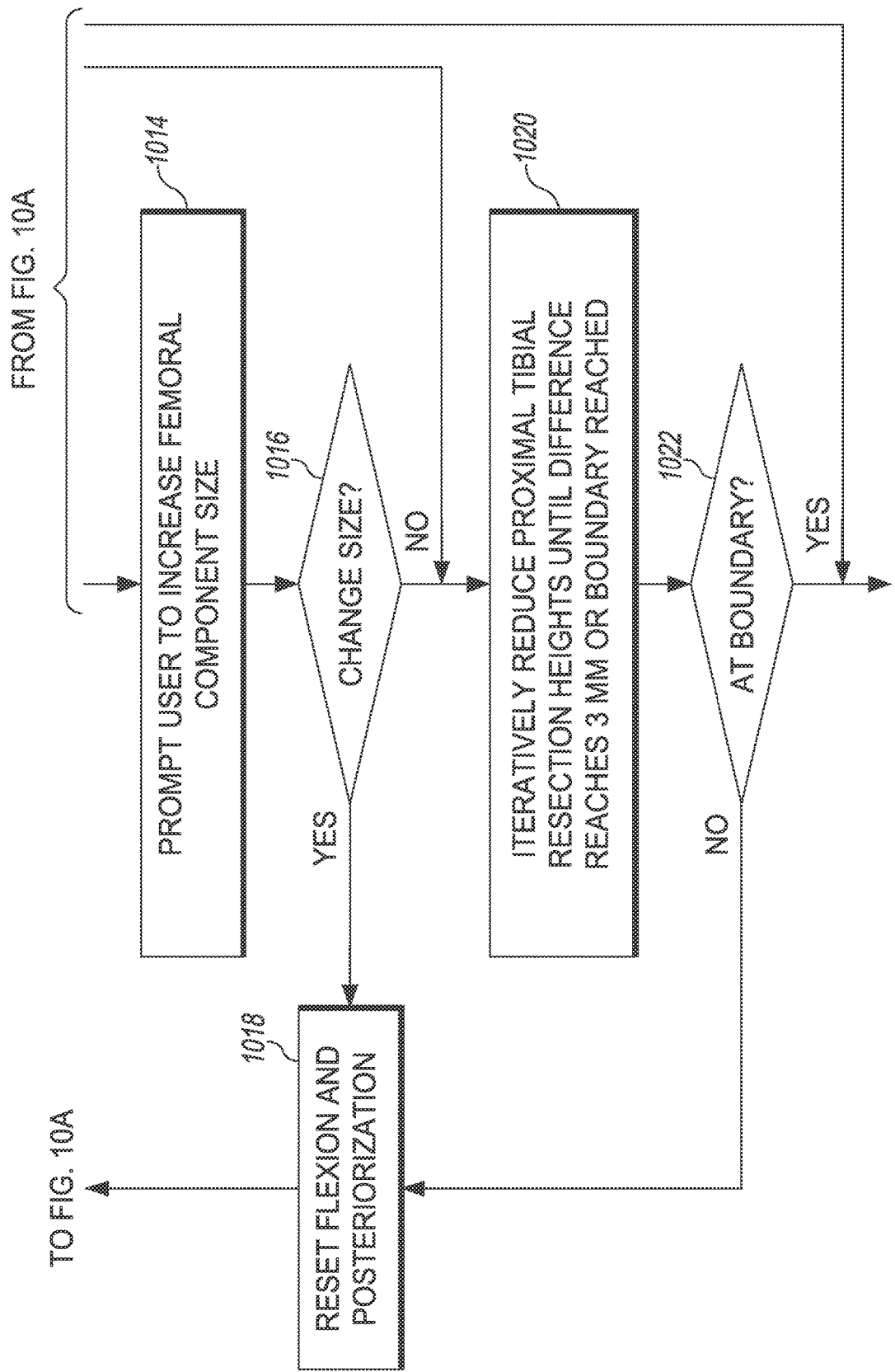

SYSTEMS AND METHODS FOR PLANNING AND ASSISTING ORTHOPAEDIC SURGICAL PROCEDURES

TECHNICAL FIELD

The present disclosure relates generally to orthopaedic surgical tools and systems and, more particularly, to systems and methods for automatically planning surgical parameters for use during an orthopaedic surgical procedure.

BACKGROUND

Joint arthroplasty is a well-known surgical procedure by which a diseased and/or damaged natural joint is replaced by a prosthetic joint, which may include one or more orthopaedic implants. For example, in a knee arthroplasty surgical procedure, a patient's natural knee joint is partially or totally replaced by a prosthetic knee joint. A typical prosthetic knee joint includes a tibial tray, a femoral component, and a polymer insert or bearing positioned between the tibial tray and the femoral component.

To facilitate the replacement of the natural joint with a prosthetic joint, orthopaedic surgeons may use a variety of orthopaedic surgical instruments such as, for example, surgical saws, cutting guides, reamers, broaches, drill guides, drills, positioners, insertion tools and/or other surgical instruments. For example, a surgeon may prepare a patient's tibia to receive the tibial tray by resecting the proximal femur with a surgical saw, and the surgeon may prepare the patient's femur to receive the femoral component by performing multiple resections of the distal femur with a surgical saw. A surgeon may use manual instruments such as cutting blocks or other cutting guides to perform various resections in an orthopaedic procedure. Alternatively, or in addition, a surgeon may use a computer-assisted surgical navigation system, such as a robotic-assisted surgical system, to perform the various resections in an orthopaedic procedure.

SUMMARY

According to one aspect, a method for generating a surgical plan for an orthopaedic surgical procedure may comprise receiving, by a computer system, a plurality of surgeon preferences comprising a target value and one or more boundary values associated with a surgical parameter of the orthopaedic surgical procedure. The method may further comprise performing, with the computer system, bony registration of bony anatomy of a patient. The method may also comprise performing, with the computer system, leg-alignment registration of the patient. Performing the leg-alignment registration may comprise measuring a flexion gap of a knee joint of the patient and measuring an extension gap of the knee joint. The method may additionally comprise determining, by the computer system, a surgical plan for the orthopaedic surgical procedure based on the plurality of surgeon preferences, the bony registration, and the leg-alignment registration. The surgical plan may comprise a planned value associated with the surgical parameter of the orthopaedic surgical procedure, and the planned value may be within the one or more boundary values associated with the surgical parameter.

In some embodiments, the method may further comprise presenting, by the computer system, the surgical plan to a user and receiving, by the computer system, a modification of the surgical plan in response to presenting the surgical plan. The modification may comprise an updated boundary value associated with the surgical parameter. The method may also comprise determining, by the computer system, an updated surgical plan for the orthopaedic surgical procedure based on the plurality of surgeon preferences, the bony registration, the leg-alignment registration, and the updated boundary value, wherein the updated boundary value overrides at least one of the plurality of surgeon preferences.

In some embodiments, determining the surgical plan for the orthopaedic surgical procedure may comprise automatically adjusting a tibial coronal alignment, automatically adjusting a femoral coronal alignment in response to automatically adjusting the tibial coronal alignment, automatically adjusting a femoral flexion in response to automatically adjusting the femoral coronal alignment, automatically adjusting a femoral rotation in response to automatically adjusting the femoral flexion, and automatically adjusting a distal femoral condyle resection height in response to automatically adjusting the femoral rotation.

In some embodiments, automatically adjusting the tibial coronal alignment may comprise determining an initial proximal tibia resection height based on the surgeon preferences and an estimate of cartilage loss and, while the proximal tibia resection height is within a minimum proximal tibia resection height boundary of the surgeon preferences, iteratively decreasing the proximal tibia resection height until a coronal angle of a tibia of the patient is within a tibial *varus/valgus* boundary of the surgeon preferences.

In some embodiments, automatically adjusting the femoral coronal alignment may comprise determining an initial distal femoral condyle resection height based on the surgeon preferences and an estimate of cartilage loss and, while a coronal angle of a femur of the patient is within a femoral *varus/valgus* boundary of the surgeon preferences and while a distal femoral condyle resection height is within a maximum distal femoral condyle resection height boundary of the surgeon preferences, iteratively increasing the distal femoral condyle resection height until a medial extension gap equals a lateral extension gap.

In some embodiments, automatically adjusting the femoral flexion may comprise, while a femoral component flexion/extension angle is within a femoral component flexion/extension boundary of the surgeon preferences, iteratively adjusting the femoral component flexion/extension angle until a total flexion gap equals an ideal flexion gap. The total flexion gap may comprise a sum of a lateral flexion gap and a medial flexion gap, and the ideal flexion gap may comprise a sum of a natural joint laxity in flexion and a predetermined component height. In response to the femoral component flexion/extension angle reaching the femoral component flexion/extension boundary, while a posterior femoral condyle resection height is within a posterior femoral condyle resection height boundary of the surgeon preferences, automatically adjusting the femoral flexion may also comprise iteratively adjusting a femoral component anterior/posterior shift until the total flexion gap equals the ideal flexion gap.

In some embodiments, automatically adjusting the femoral flexion may further comprise determining a difference between the total flexion gap and the ideal flexion gap in response to the posterior femoral condyle resection height reaching the posterior femoral condyle resection height boundary. Automatically adjusting the femoral flexion may also comprise determining whether the difference is greater than a predetermined length. The predetermined length may be associated with a femoral component size difference. In response to a determination that the difference is greater than the predetermined length, automatically adjusting the femoral flexion may further comprise prompting a change to a size of the femoral component. In response to a determination that the difference is not greater than the predetermined length, while the proximal tibia resection height is within a proximal tibia resection height boundary, automatically adjusting the femoral flexion may also comprise iteratively adjusting a proximal tibia resection height until the difference reaches the predetermined length. In response to a changing of the size of the femoral component or iteratively adjusting of the proximal tibia resection height, automatically adjusting the femoral flexion may further comprise resetting the femoral component flexion/extension angle and the femoral component anterior/posterior shift.

In some embodiments, when the total flexion gap is greater than the ideal flexion gap, iteratively adjusting the femoral component flexion/extension angle may comprise increasing the femoral component flexion angle, iteratively adjusting the femoral component anterior/posterior shift may comprise increasing posteriorization of the femoral component, prompting a change to the size of the femoral component may comprise prompting an increase in the size of the femoral component, and iteratively adjusting the proximal tibia resection height may comprise reducing the proximal tibia resection height.

In some embodiments, when the total flexion gap is less than the ideal flexion gap, iteratively adjusting the femoral component flexion/extension angle may comprise decreasing the femoral component flexion angle, iteratively adjusting the femoral component anterior/posterior shift may comprise increasing anteriorization of the femoral component, prompting a change to the size of the femoral component may comprise prompting a decrease in the size of the femoral component, and iteratively adjusting the proximal tibia resection height may comprise increasing the proximal tibia resection height.

In some embodiments, automatically adjusting the femoral rotation may comprise iteratively rotating a femoral component while a posterior femoral condyle resection height is within a posterior femoral condyle resection height boundary until medial and lateral flexion gaps equal target medial and lateral flexion gaps, respectively.

In some embodiments, automatically adjusting the distal femoral condyle resection height may comprise iteratively adjusting a distal femoral condyle resection height while the distal femoral condyle resection height is within a distal femoral condyle resection height boundary until a total extension gap equals a total flexion gap.

According to another aspect, an orthopaedic surgical planning system may comprise a computer system configured to receive a plurality of surgeon preferences comprising a target value and one or more boundary values associated with a surgical parameter of an orthopaedic surgical procedure, obtain registration data relating to a knee joint of a patient, wherein the registration data defines a flexion gap of the knee joint and an extension gap of the knee joint, and determine a surgical plan for the orthopaedic surgical procedure based on the plurality of surgeon preferences and the registration data, wherein the surgical plan comprises a planned value associated with the surgical parameter of the orthopaedic surgical procedure, and wherein the planned value is within the one or more boundary values associated with the surgical parameter.

In some embodiments, the orthopaedic surgical planning system may further comprise a registration tool configured to be positioned relative to a plurality of anatomical landmarks of the patient while observed by the computer system to obtain the registration data. The orthopaedic surgical planning system may also comprise a robotic surgical device configured to position a cutting tool for resecting a bone of the patient in order to achieve the planned value of the surgical plan.

In some embodiments, the computer system may be further configured to present the surgical plan to a user, receive a modification of the surgical plan in response to presenting the surgical plan, wherein the modification comprises an updated boundary value associated with the surgical parameter, and determine an updated surgical plan for the orthopaedic surgical procedure based on the plurality of surgeon preferences, the registration data, and the updated boundary value, wherein the updated boundary value overrides at least one of the plurality of surgeon preferences.

In some embodiments, the computer system may be configured to determine the surgical plan for the orthopaedic surgical procedure by automatically adjusting a tibial coronal alignment, automatically adjusting a femoral coronal alignment in response to automatically adjusting the tibial coronal alignment, automatically adjusting a femoral flexion in response to automatically adjusting the femoral coronal alignment, automatically adjusting a femoral rotation in response to automatically adjusting the femoral flexion, and automatically adjusting a distal femoral condyle resection height in response to automatically adjusting the femoral rotation.

In some embodiments, the computer system may be configured to automatically adjust the tibial coronal alignment by determining an initial proximal tibia resection height based on the surgeon preferences and an estimate of cartilage loss and, while the proximal tibia resection height is within a minimum proximal tibia resection height boundary of the surgeon preferences, iteratively decreasing the proximal tibia resection height until a coronal angle of a tibia of the patient is within a tibial *varus/valgus* boundary of the surgeon preferences.

In some embodiments, the computer system may be configured to automatically adjust the femoral coronal alignment by determining an initial distal femoral condyle resection height based on the surgeon preferences and an estimate of cartilage loss and, while a coronal angle of a femur of the patient is within a femoral *varus/valgus* boundary of the surgeon preferences, and while a distal femoral condyle resection height is within a maximum distal femoral condyle resection height boundary of the surgeon preferences, iteratively increasing the distal femoral condyle resection height until a medial extension gap equals a lateral extension gap.

In some embodiments, the computer system may be configured to automatically adjust the femoral flexion by, while a femoral component flexion/extension angle is within a femoral component flexion/extension boundary of the surgeon preferences, iteratively adjusting the femoral component flexion/extension angle until a total flexion gap equals an ideal flexion gap. The total flexion gap may comprise a sum of a lateral flexion gap and a medial flexion gap, and the ideal flexion gap may comprise a sum of a natural joint laxity in flexion and a predetermined component height. The computer system may further be configured to automatically adjust the femoral flexion by, in response to the femoral component flexion/extension angle reaching the femoral component flexion/extension boundary, while a posterior femoral condyle resection height is within a posterior femoral condyle resection height boundary of the surgeon preferences, iteratively adjusting a femoral component anterior/posterior shift until the total flexion gap equals the ideal flexion gap.

In some embodiments, the computer system may be configured to automatically adjust the femoral rotation by iteratively rotating a femoral component while a posterior femoral condyle resection height is within a posterior femoral condyle resection height boundary until medial and lateral flexion gaps equal target medial and lateral flexion gaps, respectively.

In some embodiments, the computer system may be configured to automatically adjust the distal femoral condyle resection height by iteratively adjusting a distal femoral condyle resection height while the distal femoral condyle resection height is within a distal femoral condyle resection height boundary until a total extension gap equals a total flexion gap.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements. The detailed description particularly refers to the accompanying figures in which:

FIGS. 10A and 10B are a simplified flow diagram of a method for automatically adjusting femoral flexion and posteriorization that may be performed by the surgical planning and assistance device of FIGS. 1-2;

DETAILED DESCRIPTION OF THE DRAWINGS

Figure 1:
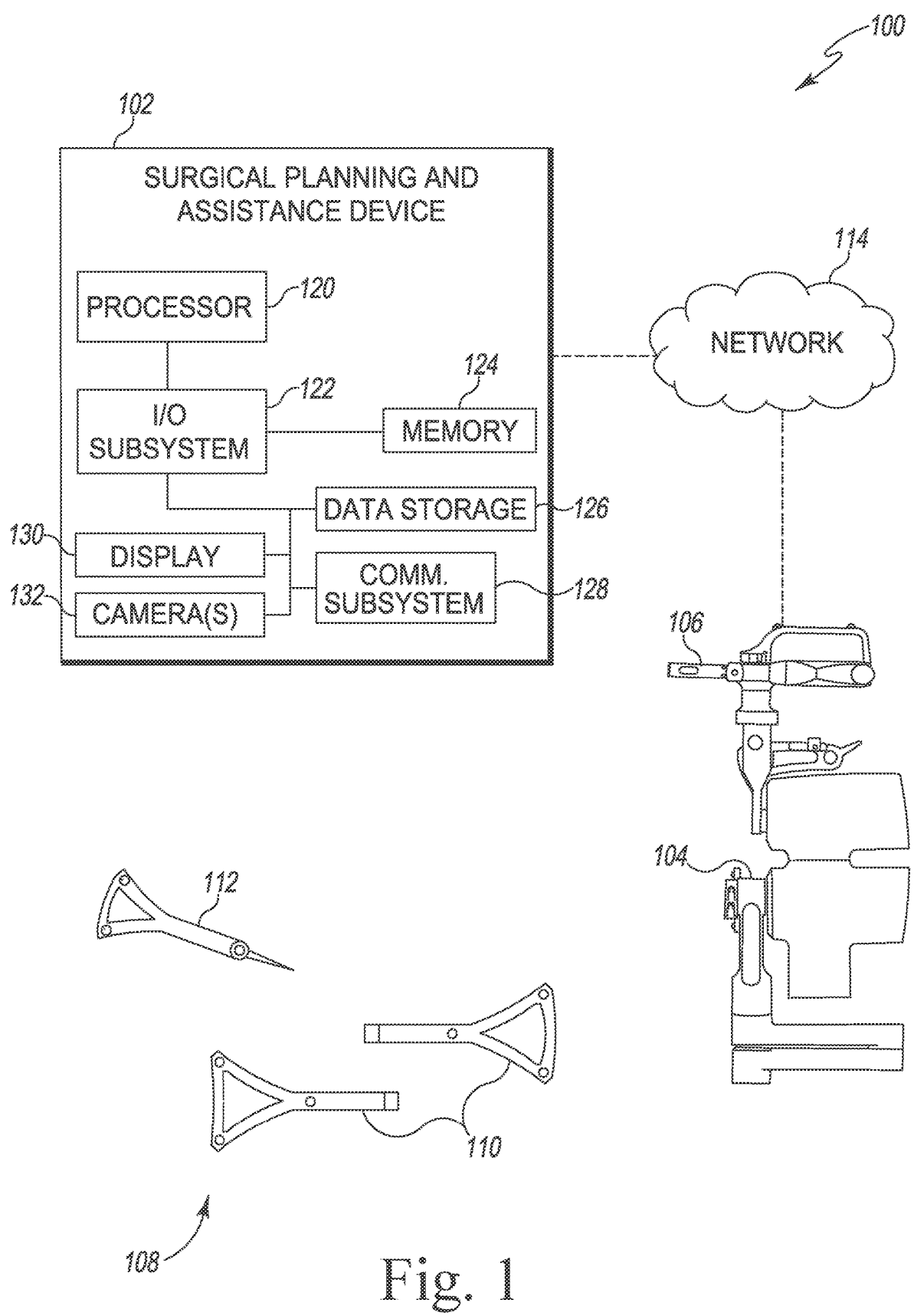
FIG. 1 is a schematic diagram of a system for planning and assisting an orthopaedic surgical procedure.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, a surgical system 100 is used during an orthopaedic surgical procedure, which is illustratively a total knee arthroplasty (TKA) procedure. During that procedure, an orthopaedic surgeon performs registration of the patient's anatomy with the system 100. The surgeon or other user uses a surgical planning and assistance device 102 to automatically create a surgical plan based on one or more surgeon preferences (which may be developed ahead of time) and the registration data. The surgeon may adjust one or more parameters of the surgical plan, and the surgical planning and assistance device 102 automatically adjusts the remaining parameters. A robotic surgical device 104 may be controlled based on the surgical plan during operation of the surgical procedure, for example by robotically constraining a surgical saw 106 to one or more resection planes defined by the surgical plan.

Thus, the system 100 provides improved automated surgical planning. The system 100 may determine a complete surgical plan more quickly and/or with less user intervention as compared to systems that require the surgeon to directly position or otherwise adjust the resection planes. Thus, the system 100 may provide for faster surgical planning and/or faster iteration times for surgical planning as compared to typical surgical planning systems.

As shown in FIG. 1, the system 100 includes the surgical planning and assistance device 102 and the robotic surgical device 104 as well as multiple registration targets 108. The surgical planning and assistance device 102 may be embodied as any type of computer system capable of performing the functions described herein. For example, the surgical planning and assistance device 102 may be embodied as, without limitation, a workstation, a desktop computer, a laptop computer, a special-purpose compute device, a server, a rack-mounted server, a blade server, a network appliance, a web appliance, a tablet computer, a smartphone, a consumer electronic device, a distributed computing system, a multiprocessor system, and/or any other computing device capable of performing the functions described herein. Additionally, although the surgical planning and assistance device 102 is illustrated in FIG. 1 as embodied as a single computer, it should be appreciated that the surgical planning and assistance device 102 may be embodied as multiple devices cooperating together to facilitate the functionality described below. For example, in some embodiments the system 100 may include a base station and a satellite station or other combination of computing devices. Additionally or alternatively, in some embodiments, the surgical planning and assistance device 102 may be embodied as a "virtual server" formed from multiple computer systems distributed across a network and operating in a public or private cloud.

As shown in FIG. 1, the illustrative surgical planning and assistance device 102 includes a processor 120, an I/O subsystem 122, memory 124, a data storage device 126, and a communication subsystem 128. Of course, the surgical planning and assistance device 102 may include other or additional components, such as those commonly found in a computer (e.g., various input/output devices), in other embodiments. Additionally, in some embodiments, one or more of the illustrative components may be incorporated in, or otherwise form a portion of, another component. For example, the memory 124, or portions thereof, may be incorporated in the processor 120 in some embodiments.

The processor 120 may be embodied as any type of processor or controller capable of performing the functions described herein. For example, the processor may be embodied as a single or multi-core processor(s), digital signal processor, microcontroller, or other processor or processing/controlling circuit. Similarly, the memory 124 may be embodied as any type of volatile or non-volatile memory or data storage capable of performing the functions described herein. In operation, the memory 124 may store various data and software used during operation of the surgical planning and assistance device 102 such as operating systems, applications, programs, libraries, and drivers. The memory 124 is communicatively coupled to the processor 120 via the I/O subsystem 122, which may be embodied as circuitry and/or components to facilitate input/output operations with the processor 120, the memory 124, and other components of the surgical planning and assistance device 102. For example, the I/O subsystem 122 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 122 may form a portion of a system-on-a-chip (SoC) and be incorporated, along with the processor 120, the memory 124, and other components of the surgical planning and assistance device 102, on a single integrated circuit chip.

The data storage device 126 may be embodied as any type of device or devices configured for short-term or long-term storage of data such as, for example, memory devices and circuits, memory cards, hard disk drives, solid-state drives, or other data storage devices. The communication subsystem 128 of the surgical planning and assistance device 102 may be embodied as any communication circuit, device, or collection thereof, capable of enabling communications between the surgical planning and assistance device 102 and remote devices. The communication subsystem 128 may be configured to use any one or more communication technology (e.g., wireless or wired communications) and associated protocols (e.g., Ethernet, Bluetooth®, Wi-Fi®, WiMAX, etc.) to effect such communication.

As shown in FIG. 1, the surgical planning and assistance device 102 includes a display 130. The display 130 may be embodied as any type of display capable of displaying digital images or other information, such as a liquid crystal display (LCD), a light emitting diode (LED), a plasma display, a cathode ray tube (CRT), or other type of display device. In some embodiments, the display 130 may be coupled to a touch screen to allow user interaction with the surgical planning and assistance device 102.

The surgical planning and assistance device 102 further includes one or more cameras 132. Each of the cameras 132 may be embodied as a digital camera or other digital imaging device coupled to the surgical planning and assistance device 102. Each camera 132 includes an electronic image sensor, such as an active-pixel sensor (APS), e.g., a complementary metal-oxide-semiconductor (CMOS) sensor, or a charge-coupled device (CCD). In the illustrative embodiment, multiple cameras 132 are arranged in an array and are thus capable of determining distance to objects imaged by the cameras 132.

The robotic surgical device 104 may be embodied as any type of robot capable of performing the functions described herein. Illustratively, the robotic surgical device 104 is embodied as a robotic arm that may be attached to a surgical table or otherwise positioned near a patient during the orthopaedic surgical procedure. The robotic surgical device 104 includes a surgical tool 106, illustratively embodied as a surgical saw 106. In use, the robotic surgical device 104 supports the surgical saw 106 and may constrain movement of the surgical saw 106 within a resection plane specified in a surgical plan, as described further below. The surgeon may activate the surgical saw 106 and perform the resection with the surgical saw 106 while the robotic surgical device 104 constrains movement of the surgical saw 106 to the resection plane. Although illustrated with a surgical saw 106, it should be understood that, in other embodiments, the robotic surgical device 104 may include, or be used with, one or more other surgical instruments, such as, for example, surgical burrs, impactors, reamers, and other powered surgical tools. The robotic surgical device 104 may illustratively be embodied as a VELYS™ Robotic-Assisted Solution, commercially available from DePuy Synthes Products, Inc. of Warsaw, Indiana.

The surgical planning and assistance device 102 and the robotic surgical device 104 may be configured to transmit and receive data with each other and/or other devices of the system 100 over a network 114. The network 114 may be embodied as any number of various wired and/or wireless networks. For example, the network 114 may be embodied as, or otherwise include, a wired or wireless local area network (LAN), a wired or wireless wide area network (WAN), a cellular network, and/or a publicly-accessible, global network such as the Internet. As such, the network 114 include any number of additional devices, such as additional computers, routers, stations, and switches, to facilitate communications among the devices of the system 100.

As shown in FIG. 1, the system 100 further includes a number of registration tools 108. As described further below, in use, the surgical planning and assistance device 102 may track the location of the registration tools 108 in space using the array of cameras 132. For example, each registration tool 108 may include a number of hydrophobic optical reflectors arranged in a predetermined pattern visible to the cameras 132. Illustratively, the registration tools 108 include a plurality of arrays 110 configured to each be secured to one of the patient's bones, to the robotic surgical device 104, or to the surgical tool 106. Illustratively, the registration tools 108 also include a pointer 112 configured to be temporarily positioned by a surgeon relative to anatomical landmarks of the patient (e.g., with an end of the pointer 112 in contact those anatomical landmarks) while the pointer 112 is observed by the cameras 132. As such, the registration tools 108 may be used for registration and tracking of the patient's bony anatomy during the orthopaedic surgical procedure.

Figure 2:
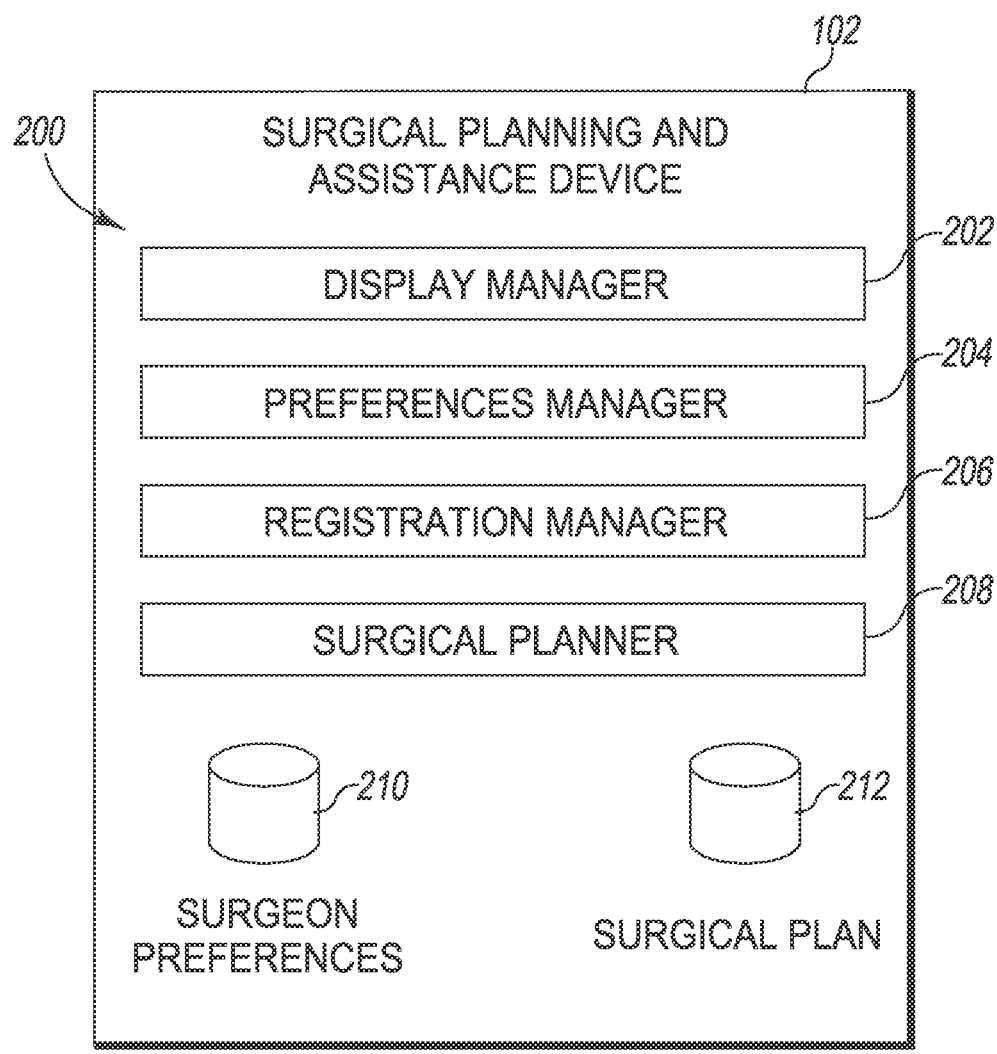
FIG. 2 is a simplified block diagram of an environment that may be established by a surgical planning and assistance device of the system of FIG. 1.

Referring now to FIG. 2, in an illustrative embodiment, the surgical planning and assistance device 102 establishes an environment 200 during operation. The illustrative environment 200 includes a display manager 202, a preferences manager 204, a registration manager 206, and a surgical planner 208. The various components of the environment 200 may be embodied as hardware, firmware, software, or a combination thereof. As such, in some embodiments, one or more of the components of the environment 200 may be embodied as circuitry or collection of electrical devices (e.g., display manager circuitry 202, preferences manager circuitry 204, registration manager circuitry 206, and/or surgical planner circuitry 208). It should be appreciated that, in such embodiments, one or more of those components may form a portion of the processor 120, the memory 124, the data storage 126, and/or other components of the surgical planning and assistance device 102.

The preferences manager 204 is configured to receive surgeon preferences 210. The surgeon preferences 210 include a target value and one or more boundary values associated with each surgical parameter of an orthopaedic surgical procedure, such as total knee arthroplasty. The surgical parameters may include resection heights, prosthetic component angles, alignment angles, or other parameters associated with the orthopaedic surgical procedure.

The registration manager 206 is configured to perform bony registration of bony anatomy of the patient and to perform leg-alignment registration of the patient. Performing the bony registration includes receiving an estimate of cartilage loss. Performing the bony registration may also include confirming a predetermined implant size. Performing the leg-alignment registration includes measuring a flexion gap of a knee joint of the patient and an extension gap of the knee joint. Measuring the flexion gap and the extension gap may include tracking multiple reflection targets 108 coupled to the bony anatomy of the patient using the camera 132 coupled to the surgical planning and assistance device 102.

The surgical planner 208 is configured to determine a surgical plan 212 for the orthopaedic surgical procedure based on the surgeon preferences 210, the bony registration, and the leg-alignment registration. The surgical plan 212 includes a planned value associated with each surgical parameter of the orthopaedic surgical procedure. Each planned value may be within the one or more boundary values associated with the surgical parameter from the surgeon preferences 210. The surgical planner 208 may be further configured to determine an updated surgical plan 212 based on the surgeon preferences 210, the leg-alignment registration, and an updated boundary value. The updated boundary value overrides the surgeon preferences 210. The surgical planner 208 may be further configured to control the robotic surgical device 104 to assist in achieving one or more planned values of the surgical plan 212. Controlling the robotic surgical device 104 may include robotically constraining the surgical saw 106 in a geometric plane defined by one or more planned values of the surgical plan 212 and the bony registration.

Determining the surgical plan 212 for the orthopaedic surgical procedure may include automatically adjusting a tibial coronal alignment, automatically adjusting a femoral coronal alignment in response to automatically adjusting the tibial coronal alignment, automatically adjusting femoral flexion in response to automatically adjusting the femoral coronal alignment, automatically adjusting femoral rotation in response to automatically adjusting the femoral flexion; and automatically adjusting distal femoral condyle resection height in response to automatically adjusting the femoral rotation.

In some embodiments, automatically adjusting the tibial coronal alignment may include determining an initial proximal tibia resection height based on the surgeon preferences 210 and the estimate of cartilage loss, and, while the proximal tibia resection height is within a minimum proximal tibia resection height boundary of the surgeon preferences 210, iteratively decreasing the proximal tibia resection height until a coronal angle of a tibia of the patient is within a tibial *varus/valgus* boundary of the surgeon preferences 210. The proximal tibia resection height may be a medial or a lateral proximal tibia resection height. In some embodiments, automatically adjusting the tibial coronal alignment may include determining a high side of either the medial side or the lateral side based on the bony registration and decreasing the proximal tibia resection height of the side other than the high side.

In some embodiments, automatically adjusting the femoral coronal alignment may include determining an initial distal femoral condyle resection height based on the surgeon preferences 210 and the estimate of cartilage loss, and iteratively increasing the distal femoral condyle resection height until a medial extension gap equals a lateral extension gap, while a coronal angle of a femur of the patient and a distal femoral condyle resection height are within boundaries of the surgeon preferences 210. Automatically adjusting the femoral coronal alignment may further include determining a smaller side of the medial extension gap and the lateral extension gap and increasing the distal femoral condyle resection height for the smaller side.

In some embodiments, automatically adjusting the femoral flexion may include iteratively adjusting a femoral component flexion/extension angle until a total flexion gap equals an ideal flexion gap while the femoral component flexion/extension angle is within boundaries of the surgeon preferences 210. The total flexion gap is a sum of a lateral flexion gap and a medial flexion gap, and the ideal flexion gap is a sum of a natural joint laxity in flexion and a predetermined component height. If the femoral component flexion/extension angle reaches the boundary, automatically adjusting the femoral flexion may include iteratively adjusting a femoral component anterior/posterior shift until the total flexion gap equals the ideal flexion gap while a posterior femoral condyle resection height is within boundaries of the surgeon preferences 210. If the posterior femoral condyle resection height reaches the boundary, automatically adjusting the femoral flexion may include determining a difference between the total flexion gap and the ideal flexion gap and prompting to change the size of the femoral component if the difference is greater than the predetermined length. If the difference is not greater than the predetermined length, automatically adjusting the femoral flexion may include iteratively adjusting a proximal tibia resection height until the difference reaches the predetermined length while the proximal tibia resection height is within boundaries of the surgeon preferences 210. The femoral component flexion/extension angle and the femoral component anterior/posterior shift may be reset in response to changing the size of the femoral component or iteratively adjusting the proximal tibia resection height. If the total flexion gap is greater than the ideal flexion gap, iteratively adjusting the femoral component flexion/extension angle includes increasing the femoral component flexion angle, and iteratively adjusting the femoral component anterior/posterior shift comprises increase posteriorization of the femoral component. If the total flexion gap is less than the ideal flexion gap, iteratively adjusting the femoral component flexion/extension angle includes decreasing the femoral component flexion angle, and iteratively adjusting the femoral component anterior/posterior shift comprises increase anteriorization of the femoral component.

In some embodiments, automatically adjusting the femoral rotation includes iteratively rotating a femoral component until medial and lateral flexion gaps equal target medial and lateral flexion gaps, while a posterior femoral condyle resection height is within boundaries of the surgeon preferences 210. In some embodiments, automatically adjusting the distal femoral condyle resection height includes iteratively adjusting a distal femoral condyle resection height until a total extension gap equals a total flexion gap while the distal femoral condyle resection height is within boundaries of the surgeon preferences 210.

The display manager 202 is configured to present the surgical plan 212 to a user, such as a surgeon. The display manager 202 may be further configured to receive a modification of the surgical plan 212 in response to presenting the surgical plan 212. The modification may include an updated boundary value associated with a surgical parameter. The display manager 202 may be further configured to indicate whether one or more boundaries of the surgeon preferences 210 were reached in response to determining the surgical plan 212.

Figure 3A:
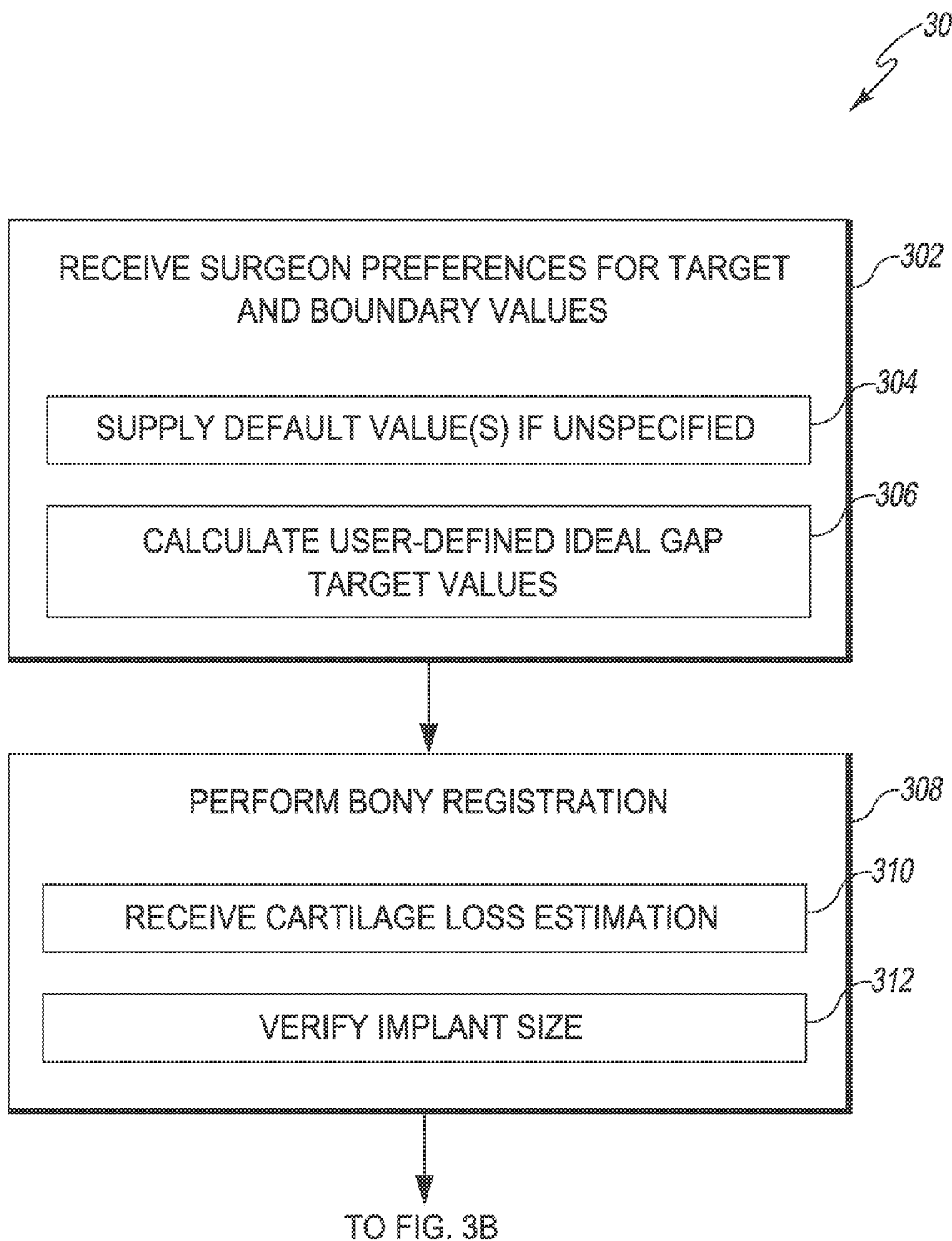
FIGS. 3A, 3B, and 3C are a simplified flow diagram of a method for an orthopaedic surgical procedure including automated surgical planning that may be executed by the surgical planning and assistance device of FIGS. 1-2.
Figure 3B:
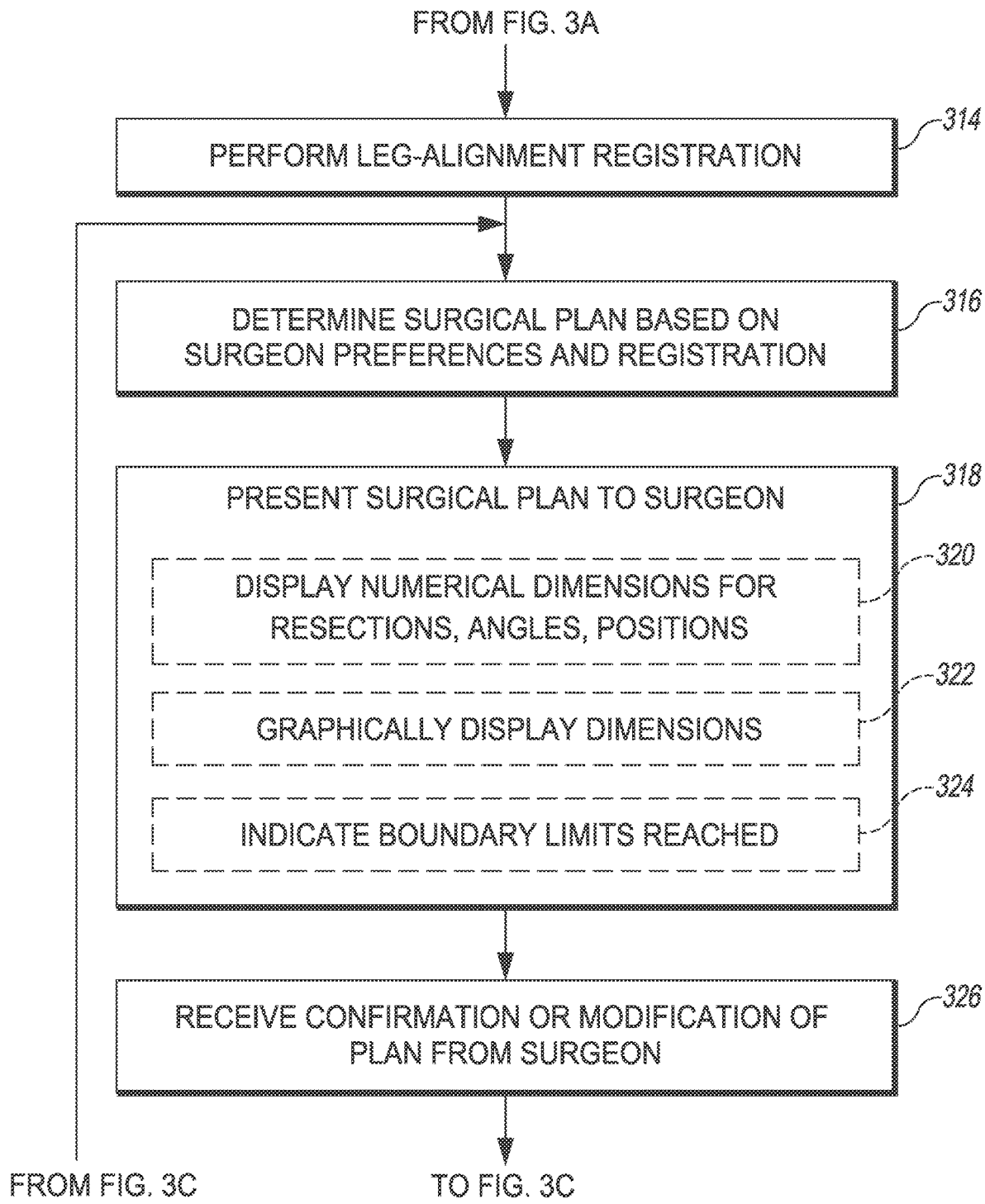
Figure 3C:
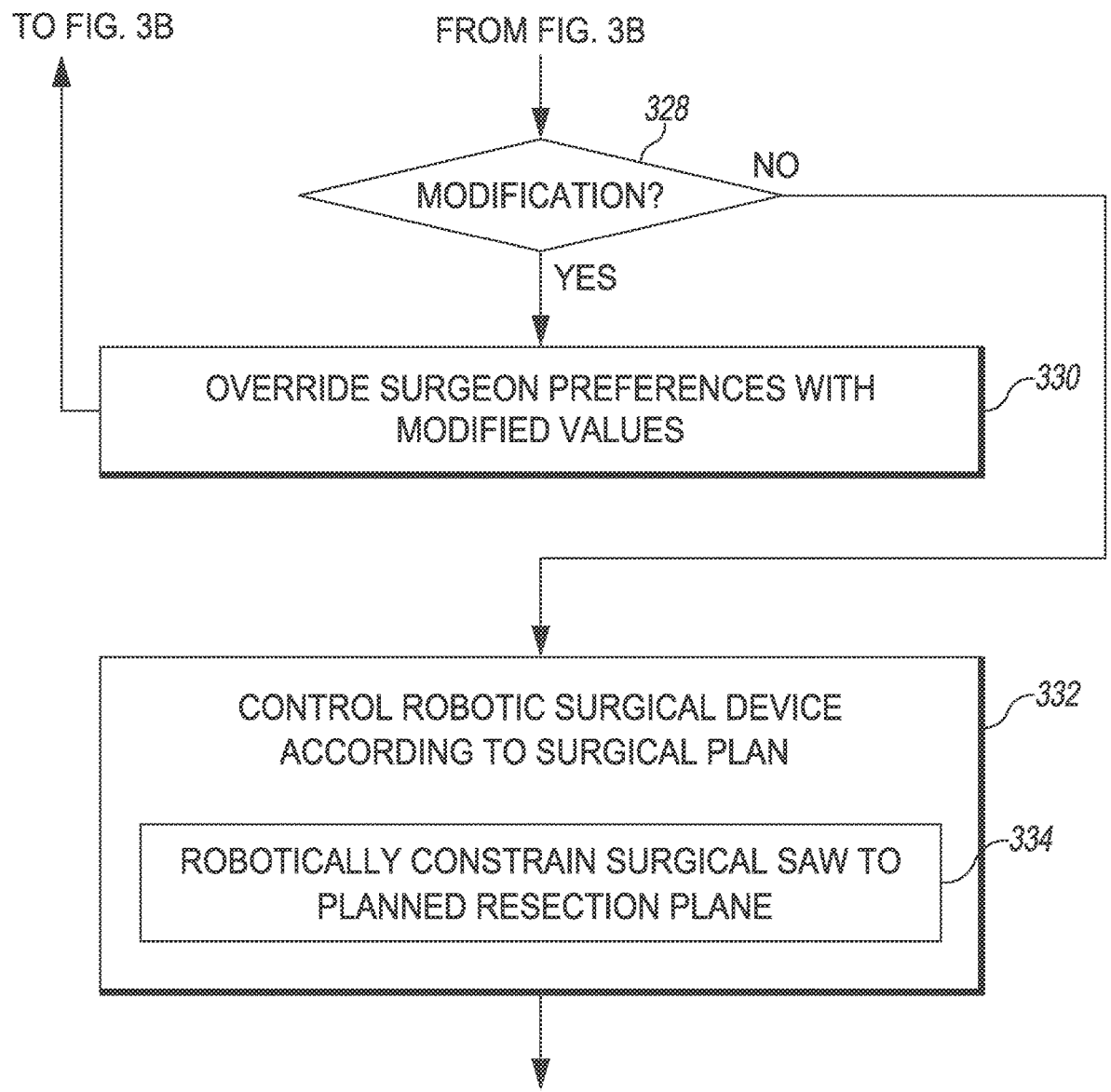

Referring now to FIG. 3, in use, the surgical planning and assistance device 102 may perform a method 300 for an orthopaedic surgical procedure with automated surgical planning. It should be appreciated that, in some embodiments, the operations of the method 300 may be performed by one or more components of the environment 200 of the surgical planning and assistance device 102 as shown in FIG. 2. The method 300 begins with block 302, in which the device 102 receives surgeon preferences 210 for targets and boundary values for various surgical parameters associated with the orthopaedic surgical procedure. For example, the surgeon preferences 210 may include target values for tibial and femoral resection heights, component angles, and other surgical parameters that affect the position of the prosthetic implant components. For each target value, the surgeon preferences 210 may include minimum and maximum values, acceptable ranges, or other boundary conditions. The surgeon preferences 210 may be input to the device 102, for example using a touch screen or other input device, or the surgeon preferences 210 may be received from a remote device. In some embodiments, the surgeon preferences 210 may be determined ahead of time and may be reused for multiple surgical procedures.

Figure 4:
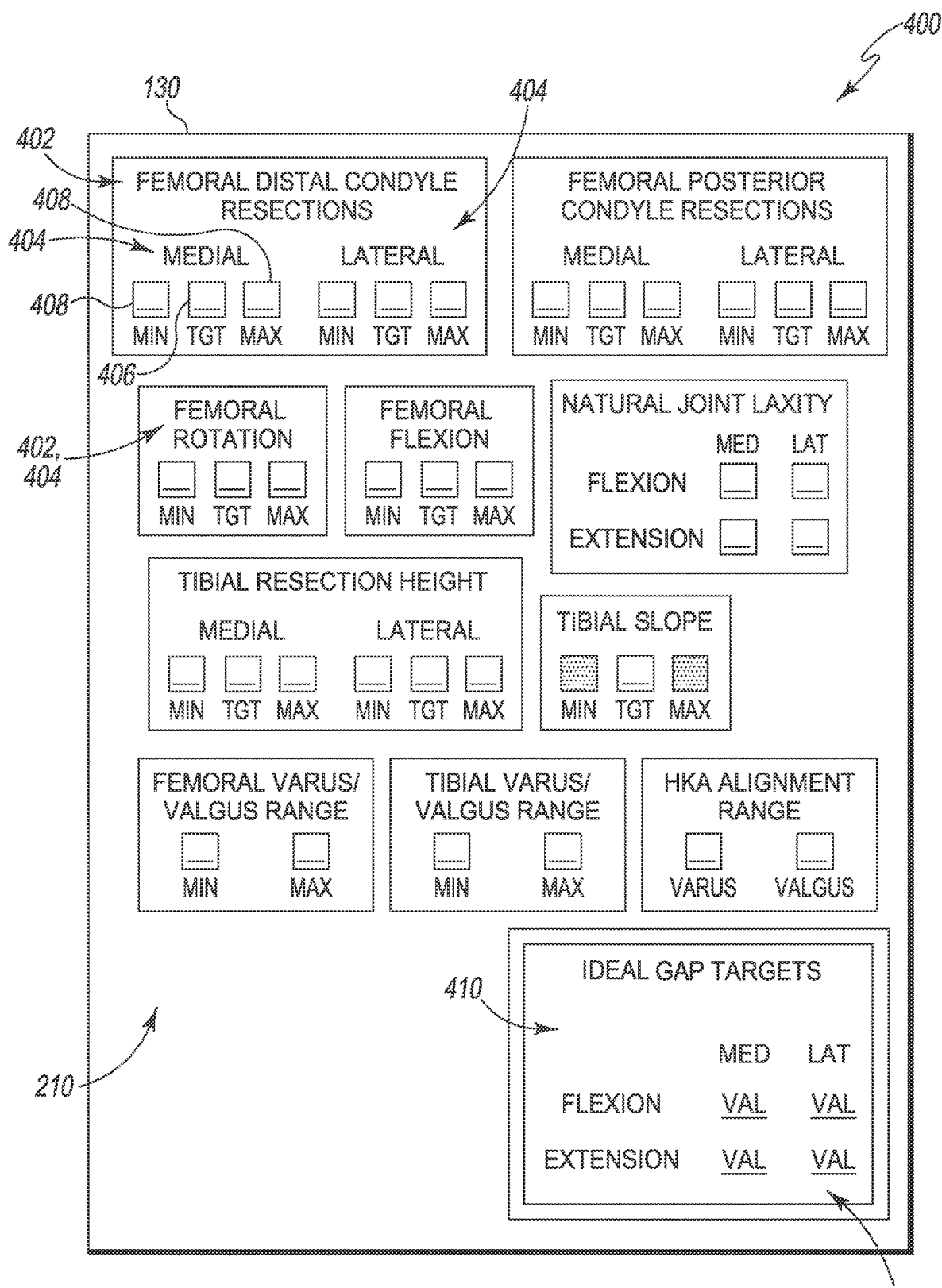
FIG. 4 is a schematic diagram illustrating surgeon preferences that may be collected and otherwise processed by the surgical planning and assistance device of FIGS. 1-2.

Referring now to FIG. 4, diagram 400 illustrates one potential embodiment of surgeon preferences 210 that may be received by the device 102. The diagram 400 illustrates a graphical user interface for viewing and/or editing the surgeon preferences 210 that may be displayed on the display 130 of the device 102. The surgeon preferences 210 are graphically organized into a number of preference groupings 402. Each preference grouping 402 contains user interface controls for one or more surgical parameters 404. For each surgical parameter 404, the surgeon may view and/or edit values for a target value 406 and/or one or more boundary values 408. Those values may be edited using text box controls as shown in FIG. 4 or using any other appropriate user interface.

The illustrative diagram 400 shows one illustrative collection of surgical parameters 404 that may be associated with surgeon preferences 210. As shown, the illustrative surgeon preferences 210 include distal femoral condyle resection heights for both the medial distal condyle and the lateral distal condyle. Each of those resection heights may include a target value as well as a minimum boundary and a maximum boundary, each of which may be measured in millimeters relative to the most-distal point of the most-distal condyle. Similarly, the illustrative surgeon preferences 210 include posterior femoral condyle resection heights for both the medial posterior condyle and the lateral posterior condyle. Each of those resection heights may include a target value as well as a minimum boundary and a maximum boundary, each of which may be measured in millimeters relative to a reference point (e.g., a point on the anterior cortex of the femur).

The illustrative surgeon preferences 210 further include femoral rotation angle, including a target value as well as a minimum boundary and a maximum boundary, each of which may be measured in degrees relative to an anatomical line (e.g., the posterior condylar axis, Whiteside's line, or the transepicondylar axis). Similarly, the illustrative surgeon preferences 210 further include femoral component flexion angle, including a target value as well as a minimum boundary and a maximum boundary, each of which may be measured in degrees relative to a reference axis (e.g., the sagittal mechanical axis of the femur).

The illustrative surgeon preferences 210 further include values for natural joint laxity for the knee in flexion and in extension, for both the medial and lateral sides. Those preferences may each include a target value measured in millimeters.

The illustrative surgeon preferences 210 further include proximal tibia resection heights for both the medial side and the lateral side. Each of those resection heights may include a target value as well as a minimum boundary and a maximum boundary, each of which may be measured in millimeters relative to the high side of the tibia. The illustrative surgeon preferences 210 further include tibial slope, which illustratively includes a target value measured in degrees. In other embodiments, the surgeon preferences 210 may include minimum and maximum boundaries for tibial slope, but those boundaries are not used in the illustrative embodiment.

The illustrative surgeon preferences 210 further include a femoral *varus/valgus* range, also called a femoral coronal alignment range, which includes a minimum boundary value and a maximum boundary value measured in degrees. Similarly, the illustrative surgeon preferences 210 further include a tibial *varus/valgus* range, also called a tibial coronal alignment range, which includes a minimum boundary value and a maximum boundary value measured in degrees. Further, the illustrative surgeon preferences 210 further include a hip-knee-ankle (HKA) alignment range, also called a mechanical alignment range, which includes a minimum boundary value and a maximum boundary value measured in degrees.

The illustrative diagram 400 further includes a grouping 410 of computed values 412. The computed values 412 are generated by the device 102 based on one or more other values of the surgeon preferences 210 and are thus not directly editable. Accordingly, the computed values 412 are displayed using label controls or other read-only user interface elements. Illustratively, the computed values 412 include ideal gap targets for the joint in flexion and in extension, for both the medial side and the lateral side. As described further below, those ideal gap targets are calculated based on the natural joint laxity targets of the surgeon preferences 210.

Referring back to FIG. 3, after receiving the surgeon preferences 210 in block 302, the device 102 may supply one or more default values for target or boundary values in block 304, if the surgeon preferences 210 are not specified. In block 306, the device 102 calculates user-defined gap target values based on the surgeon preferences 210. Illustratively, each of the ideal gap targets equals the natural joint laxity provided by the user added with a predetermined value that may correspond to the type of implant being used in the surgical procedure (e.g., the component thickness of the particular implant to be used). For example, the ideal gap for the medial side in flexion may be the natural joint laxity for the medial side in flexion (provided by the user) plus eight millimeters or nine millimeters (depending on the implant in use). The other ideal gap targets may be similarly calculated.

In block 308, the device 102 may perform bony registration of the patient's bony anatomy. To perform the bony registration, the surgeon may attach a bone array 110 to each of the patient's tibia and femur. The surgeon may use the pointer 112 to touch various landmarks on the patient's bony anatomy. During the registration, the device 102 uses the cameras 132 to track the position of the bone arrays 110 and the pointer 112 and thus registers the position of each landmark of the patient's bony anatomy.

As part of bony registration, the device 102 receives a cartilage loss estimation from the surgeon or other user in block 310. The surgeon may estimate the amount of cartilage lost (in millimeters) for each of the distal medial condyle, distal lateral condyle, posterior medial condyle, posterior lateral condyle, medial tibia, and lateral tibia. The surgeon or another user may input those cartilage loss estimates to the device 102, for example using a touch screen or other input device.

In block 312, the device 102 prompts the surgeon or other user to verify an implant size to be used in the orthopaedic surgical procedure. The implant size may be predetermined during preoperative planning or otherwise set to an initial value. After prompting, the surgeon or other user may select a different implant size, which is stored by the device 102 for further processing.

Figure 5:
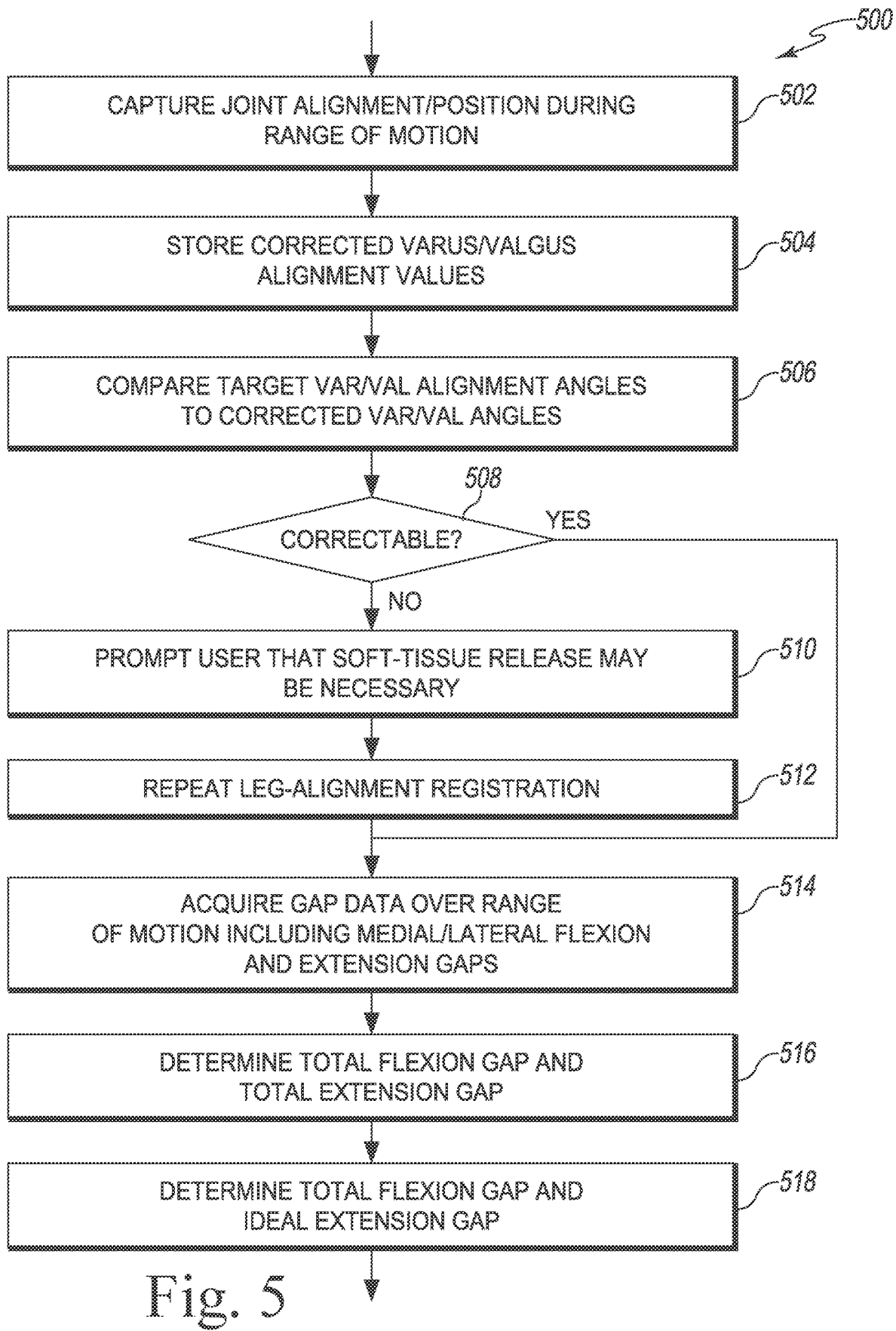
FIG. 5 is a simplified flow diagram of a method for leg-alignment registration that may be performed by the surgical planning and assistance device of FIGS. 1-2.

In block 314, the device 102 performs leg-alignment registration to assess the balance of the patient's knee joint throughout a range of motion. During block 314, the device 102 captures gap values between the patient's femur at a plurality of functional positions, including at least flexion and extension. Based on leg-alignment registration, the device 102 determines an ideal flexion gap target and an ideal extension gap target. One potential embodiment of a method for leg-alignment registration that may be executed by the device 102 is shown in FIG. 5 and described below. If the surgeon performs soft tissue release, the device 102 may repeat the leg-alignment registration.

In block 316, the device 102 determines a surgical plan 212 based on the surgeon preferences 210, the bony registration, and the leg-alignment registration. The surgical plan 212 includes a computed, planned value for each surgical parameter associated with the orthopaedic surgical procedure. As described further below, the device 102 automatically calculates the planned values using an iterative algorithm that converges on planned values that are within the boundary values specified in the surgeon preferences 210 (if possible). For example, the surgical plan may converge on planned values that equal the user-defined gap targets (e.g., medial and lateral extension and flexion gap values) or come as close as possible to the user-defined gap targets with surgical parameters within the boundary values. In some embodiments, changes to one or more surgical parameters may impact other surgical parameters, and thus the device 102 automatically updates planned values as needed. Potential embodiments for methods for automatically determining the surgical plan 212 are shown in FIGS. 6-13 and described below.

Figure 14:
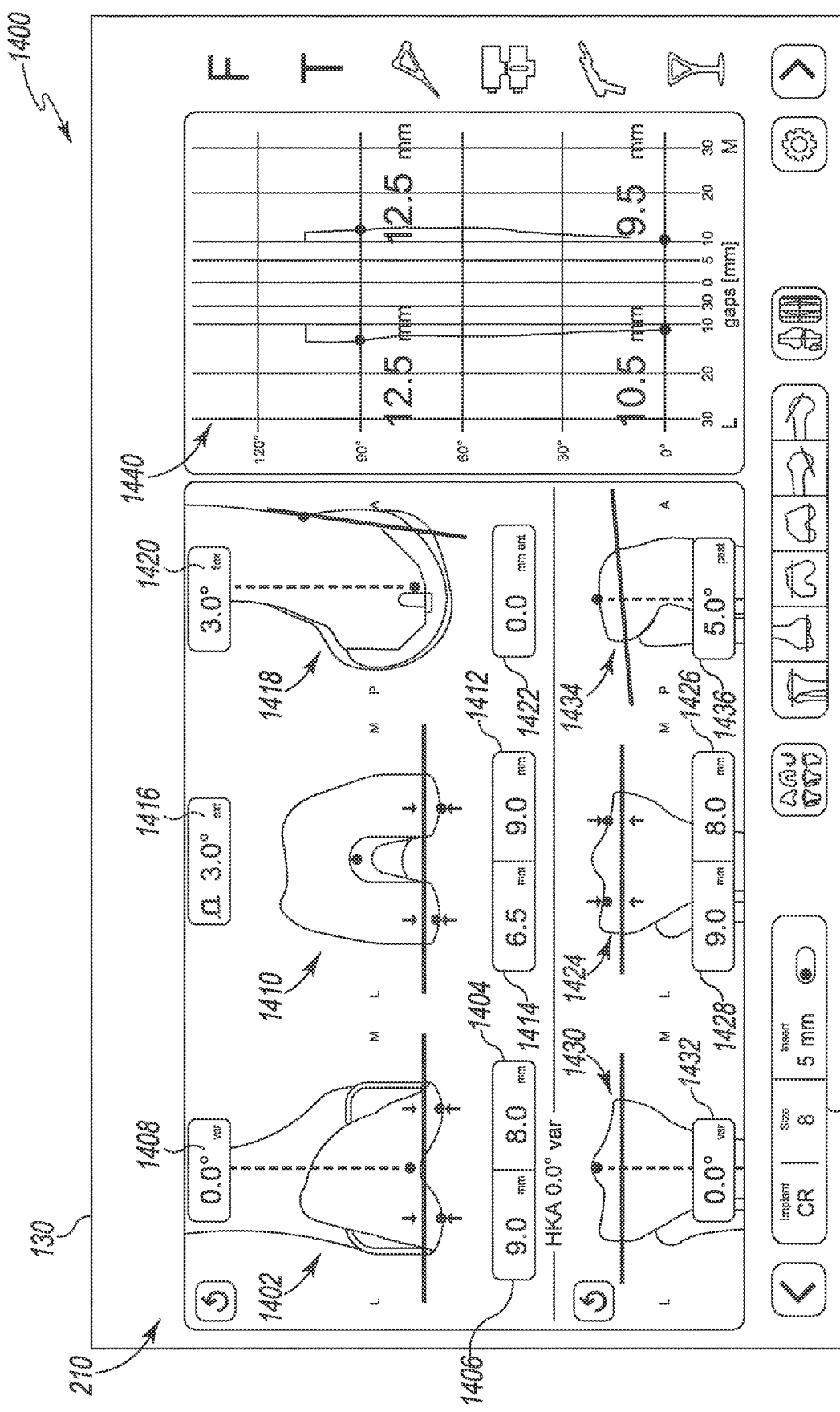
FIG. 14 is a schematic diagram of one illustrative embodiment of a graphical user interface that may be provided by the surgical planning and assistance device of FIGS. 1-2.

After generating the surgical plan 212, the device 102 presents the surgical plan 212 to the surgeon or other user in block 318. The device 102 may use any input/output device or output modality to present the surgical plan 212. In some embodiments, represented by block 320, the device 102 may display numerical dimensions for resection heights, angles, position shifts, or other parameters of the surgical plan 212 using the display 130. In some embodiments, represented by block 322, the device 102 may graphically display the dimensions of the surgical plan 212 using the display 130. For example, the device 102 may graphically render three-dimensional models of the patient's bony anatomy along with the prosthetic components that are positioned relative to the bony anatomy according to the surgical plan 212. One illustrative example of a graphical user interface that may be generated by the device 102 in blocks 320 and 322 is shown in FIG. 14 and further described below. In some embodiments, represented by block 324, the device 102 may indicate any boundary limits that were reached when generating the surgical plan 212. For example, the device 102 may highlight, outline, or otherwise emphasize any boundary limit (e.g., minimum or maximum resection height, minimum or maximum angle, etc.) that was reached during calculation of the surgical plan 212.

In block 326, the device 102 receives a confirmation or a modification of the surgical plan 212 from the surgeon. The surgeon may modify the surgical plan 212 by modifying one or more planned values of the surgical plan 212. For example, the surgeon may increase or decrease a particular resection height or may adjust a particular angle. As another example, the surgeon may modify the surgical plan 212 by modifying one or more boundary values of the surgeon preferences 210. For example, the surgeon may increase a maximum boundary that was reached or may decrease a minimum boundary that was reached. In block 328, the device 102 determines whether a modification was received. If not, the method 300 branches ahead to block 332, described below. If a modification was received, the method 300 advances to block 330.

In block 330, the device 102 overrides one or more surgeon preferences 210 with the modified values provided by the surgeon. The device 102 may, for example, override one or more boundary values of the surgeon preferences 210 in order to include the modified values specified by the surgeon. After overriding the surgeon values, the method 300 loops back to block 316, in which the device 102 re-determines the surgical plan 212 using the overridden surgeon preferences 210.

Referring back to block 328, if no modification was received, the method 300 branches to block 332, in which the device 102 controls the robotic surgical device 104 according to the surgical plan 212 to assist the surgeon in performing the orthopaedic surgical procedure. The device 102 may transmit the surgical plan 212 to the robotic surgical device 104 or otherwise cause the robotic surgical device 104 to operate according to the surgical plan 212. Illustratively, in block 334, the robotic surgical device 104 robotically constrains the surgical saw 106 to a planned resection plane according to the surgical plan 212. For example, the robotic surgical device 104 may constrain the surgical saw 106 to a resection plane defined by the medial distal femoral condyle resection height of the surgical plan 212. The robotic surgical device 104 may locate this resection plane relative to the patient's anatomy by tracking the bone array 110 using the cameras 132 of the device 102, similar to the bony registration process described above. After the surgeon completes this resection, the robotic surgical device 104 may continue to robotically constrain the surgical saw 106 for additional resections based on additional parameters of the surgical plan 212. After controlling the robotic surgical device 104, the method 300 is completed. The surgeon may continue the orthopaedic surgical procedure, for example by installing one or more trial components, one or more prosthetics, or otherwise completing the orthopaedic surgical procedure.

Referring now to FIG. 5, in use, the device 102 may perform a method 500 for leg-alignment registration. It should be appreciated that in some embodiments, the operations of the method 500 may be performed in connection with block 314 of FIG. 3, described above. The method 500 begins with block 502, in which the device 102 captures joint alignment/position of the patient while the patient's knee joint is moved through a range of motion. In particular, the surgeon may articulate the patient's knee joint through the range of motion while the device 102 uses the cameras 132 to track the position of the bone arrays 110 and thus registers the relative positions of the femur 200 and the tibia 202 at multiple points in the range of motion. While moving the knee joint through range of motion, the surgeon may apply *varus* and *valgus* stress to represent the surgeon's desired final tension in the medial and collateral ligaments. In block 504, the device 102 stores the captured alignment values as corrected *varus/valgus* alignment values.

In block 506, the device 102 compares the target *varus/valgus* alignment angles of the surgeon preferences 210 to the measured corrected *varus/valgus* angles. In particular, the device 102 determines whether the corrected alignment angles are within the target alignment angle boundaries. The device 102 may determine whether the corrected alignment angle (HKA angle) under *varus* stress is greater than or equal to the target HKA *varus* boundary (e.g., a negative number), and whether the corrected alignment angle (HKA angle) under *valgus* stress is less than or equal to the target HKA *valgus* boundary (e.g., a positive number). In block 508, the device 102 determines whether the HKA angle is correctable. The HKA angle may be correctable if the corrected *varus/valgus* angles are within the target *varus/valgus* boundary angles as determined in connection with block 506. If the alignment is correctable, the method 500 branches ahead to block 514, described below. If the alignment is not correctable, the method 500 advances to block 508.

In block 510, the device 102 prompts the surgeon or other user that soft tissue release may be necessary. The device 102 may, for example, display a message using the display 130. In block 512, the device 102 may repeat leg-alignment registration after the surgeon performs soft tissue release.

In block 514, the device 102 acquires gap data over a range of motion including medial and lateral flexion gap information and extension gap information. The surgeon may, for example, move the knee joint through its entire range of motion from extension to flexion. The surgeon may apply a *varus* force while moving the knee through the range of motion, and the surgeon may repeat moving the knee through the range of motion while applying a *valgus* force. The device 102 captures flexion and extension gap information by recording motion of the bone arrays 110 using the cameras 132 over the range of motion. Other techniques for capturing gap data over the range of motion may be employed, for example recording in extension and flexion only.

In block 516, the device 102 determines a total flexion gap and a total extension gap. The total flexion gap is the medial flexion gap added to the lateral flexion gap and, similarly, the total extension gap is the medial extension gap added to the lateral extension gap. In block 518, the device 102 determines an ideal flexion gap and an ideal extension gap. The ideal flexion gap is equal to the medial flexion gap target plus the lateral flexion gap target, and the ideal extension gap is equal to the medial extension gap target plus the lateral extension gap target. Those gap values are used during automatic determination of the surgical plan 212 as described further below. In some embodiments, the presence of recurvodum can be accounted for by subtracting 1.5 mm from the medial extension gap target and the lateral extension gap target. This function could be provided, for example, in response to a toggle switch or other user interface control that may be activated before or after the surgical plan 212 is created. After determining the ideal flexion and extension gaps, the method 500 is completed. The device 102 may continue with execution of the method 300 as shown in FIG. 3 and described above.

Figure 6:
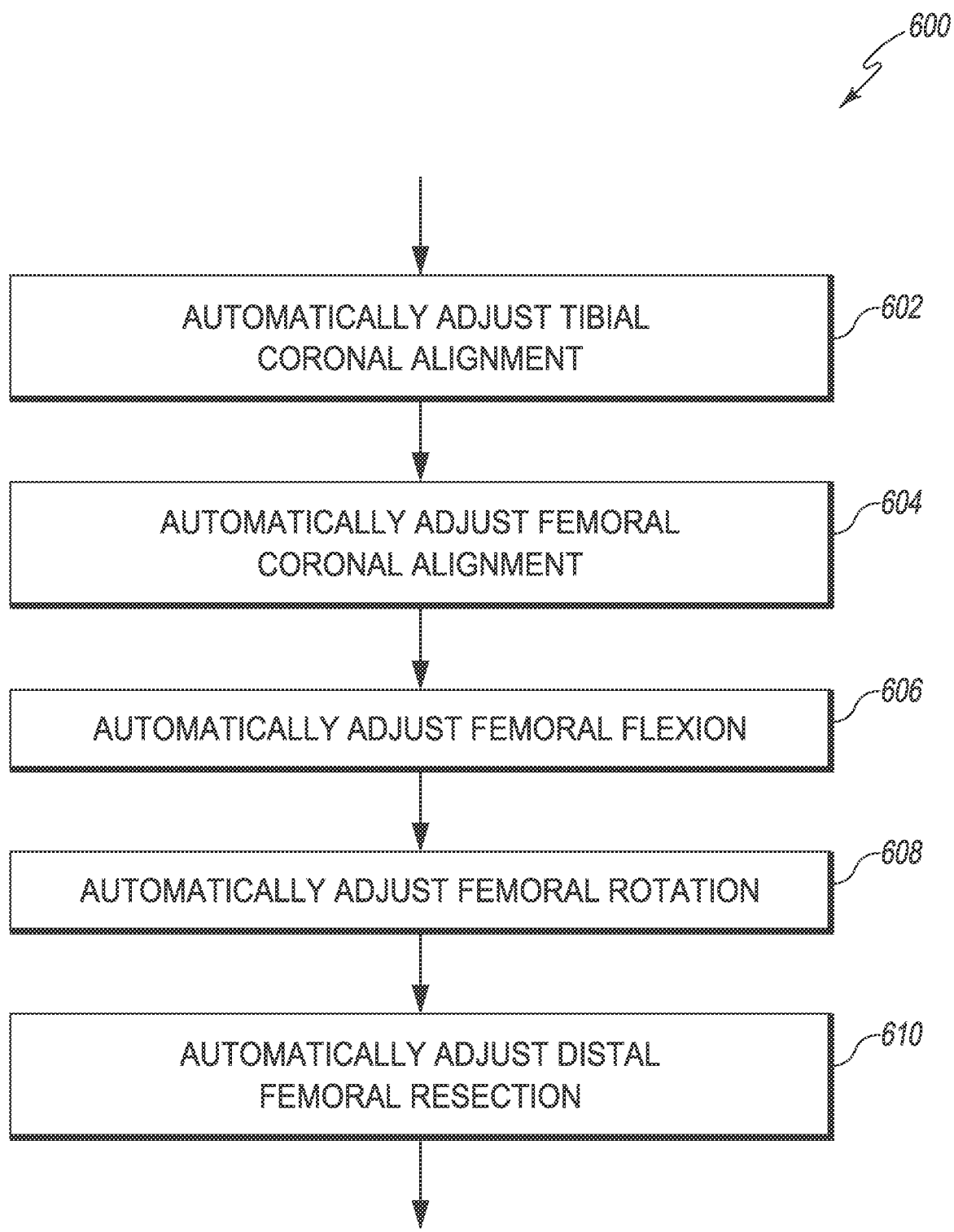
FIG. 6 is a simplified flow diagram of a method for automated surgical planning that may be performed by the surgical planning and assistance device of FIGS. 1-2.
Figure 7A:
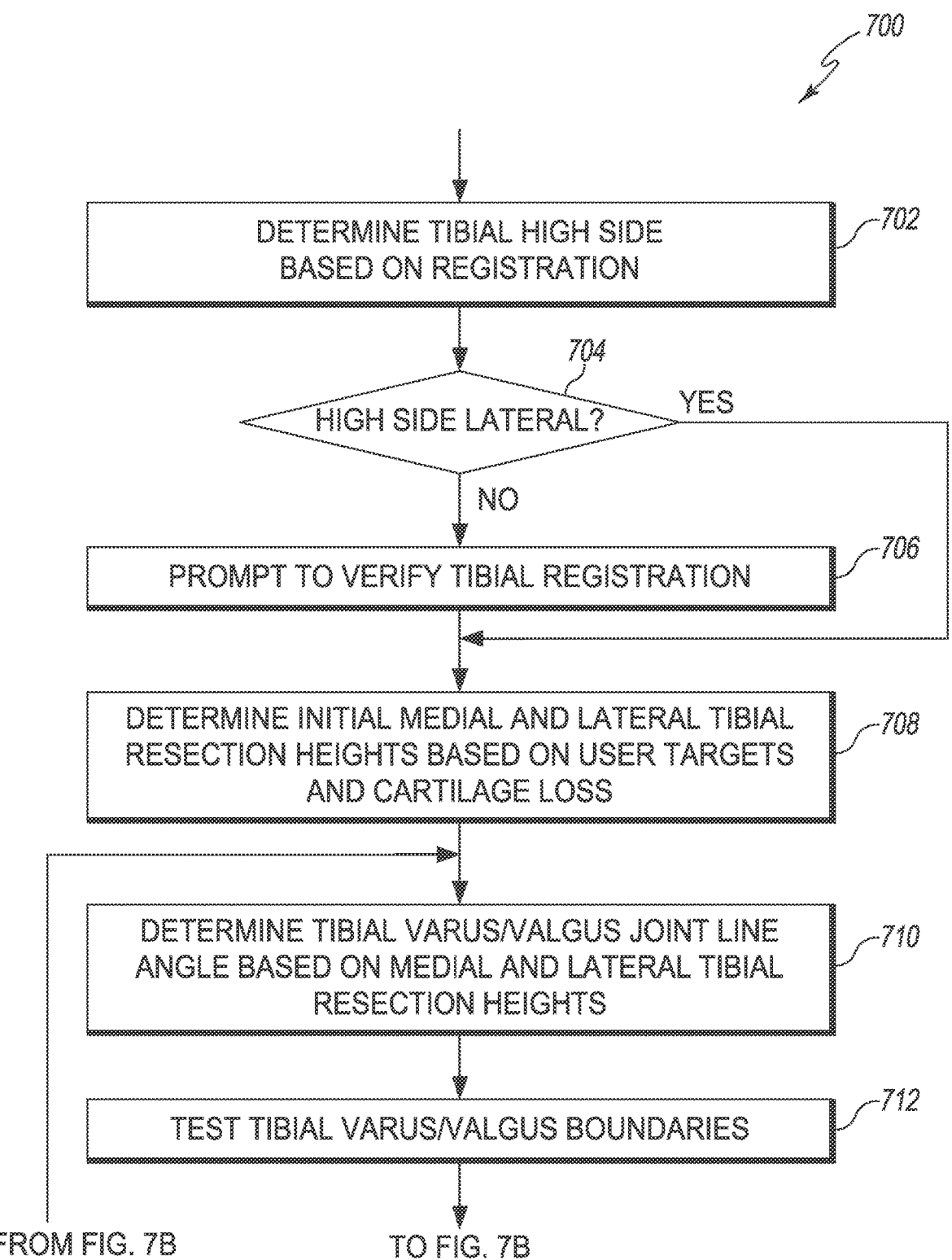
FIGS. 7A and 7B are a simplified flow diagram of a method for automatically adjusting tibial coronal alignment that may be performed by the surgical planning and assistance device of FIGS. 1-2.
Figure 7B:
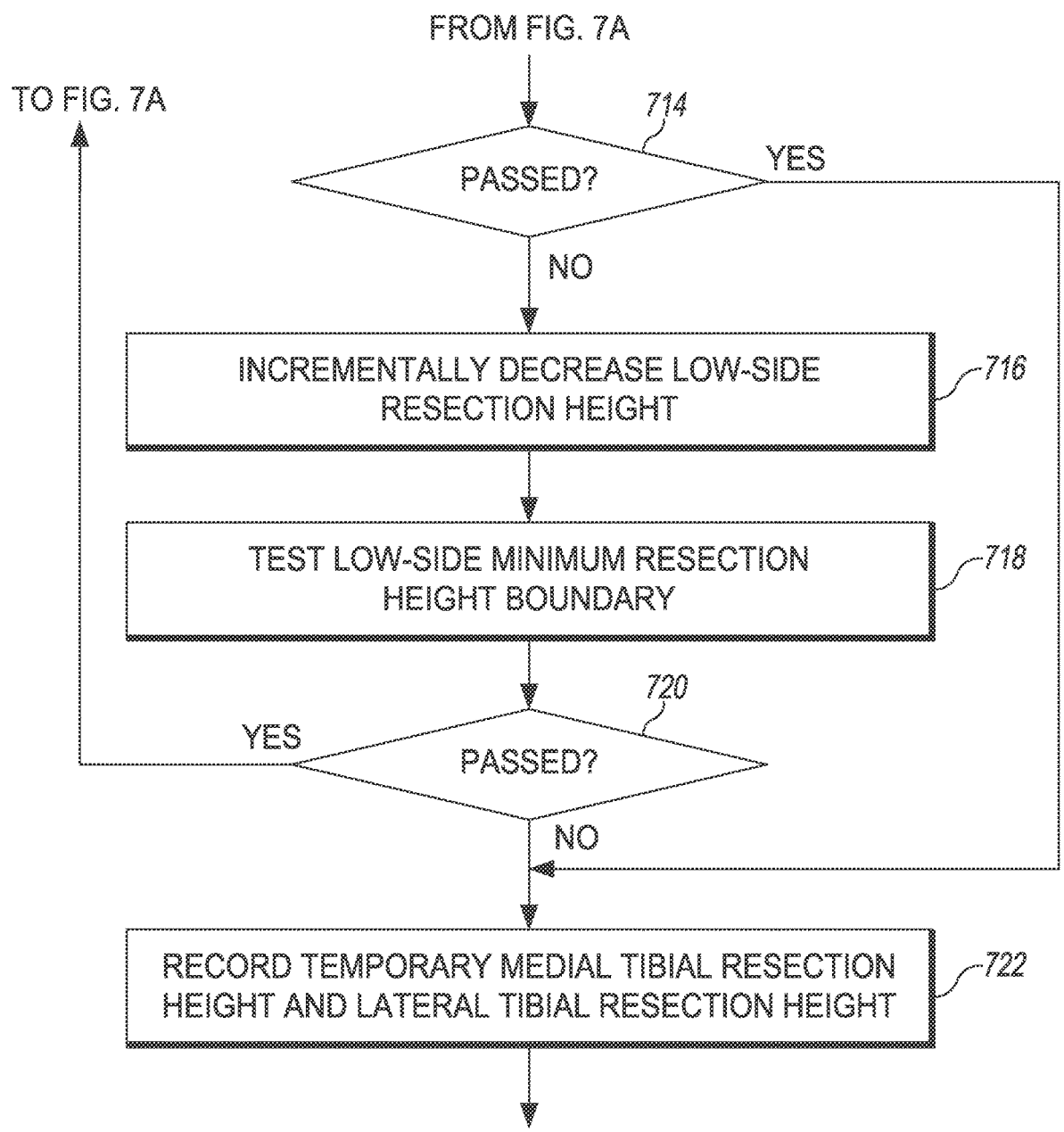

Referring now to FIG. 6, in use, the device 102 may perform a method 600 for automated surgical planning. It should be appreciated that in some embodiments, the operations of the method 600 may be performed in connection with block 316 of FIG. 3, described above. The method 600 begins with block 602, in which the device 102 automatically adjusts tibial coronal alignment in the surgical plan 212. To adjust tibial coronal alignment, the device 102 iteratively adjusts medial and lateral proximal tibia resection heights while remaining within boundaries for proximal tibia resection height and tibial *varus/valgus* angle from the surgeon preferences 210. One potential embodiment of a method for automatically adjusting tibial coronal alignment is shown in FIG. 7 and described below (see also graphical representations 1424, 1430 in FIG. 14).

Figure 8A:
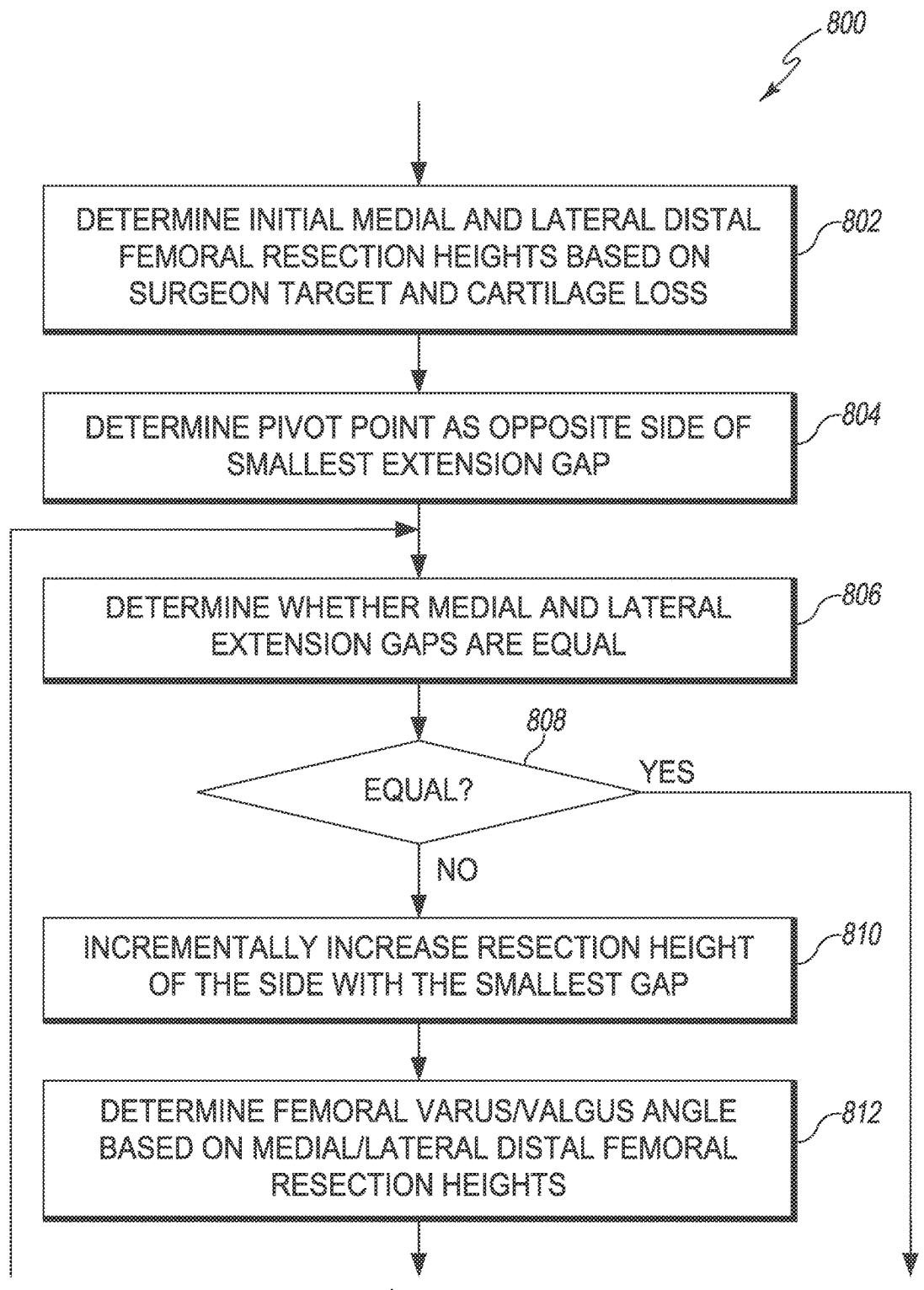
FIGS. 8A and 8B are a simplified flow diagram of a method for automatically adjusting femoral coronal alignment that may be performed by the surgical planning and assistance device of FIGS. 1-2.
Figure 8B:
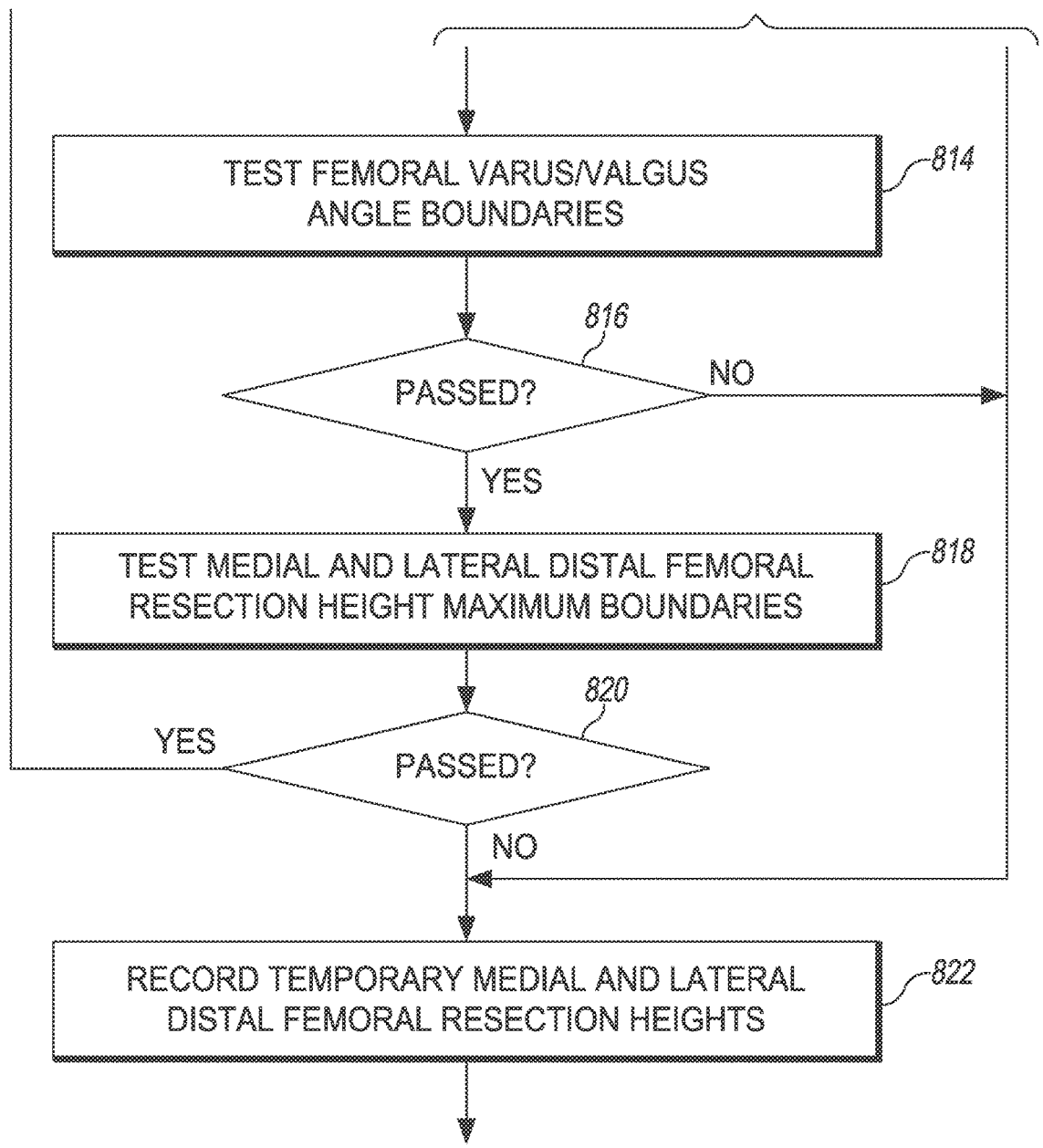

In block 604, the device 102 automatically adjusts femoral coronal alignment in the surgical plan 212. To adjust femoral coronal alignment, the device 102 iteratively adjusts medial and lateral distal femoral condyle resection heights while remaining within boundaries for distal femoral condyle resection height and femoral *varus/valgus* angle from the surgeon preferences 210. One potential embodiment for automatically adjusting femoral coronal alignment is shown in FIG. 8 and described below (see also graphical representation 1402 in FIG. 14).

Figure 9A:
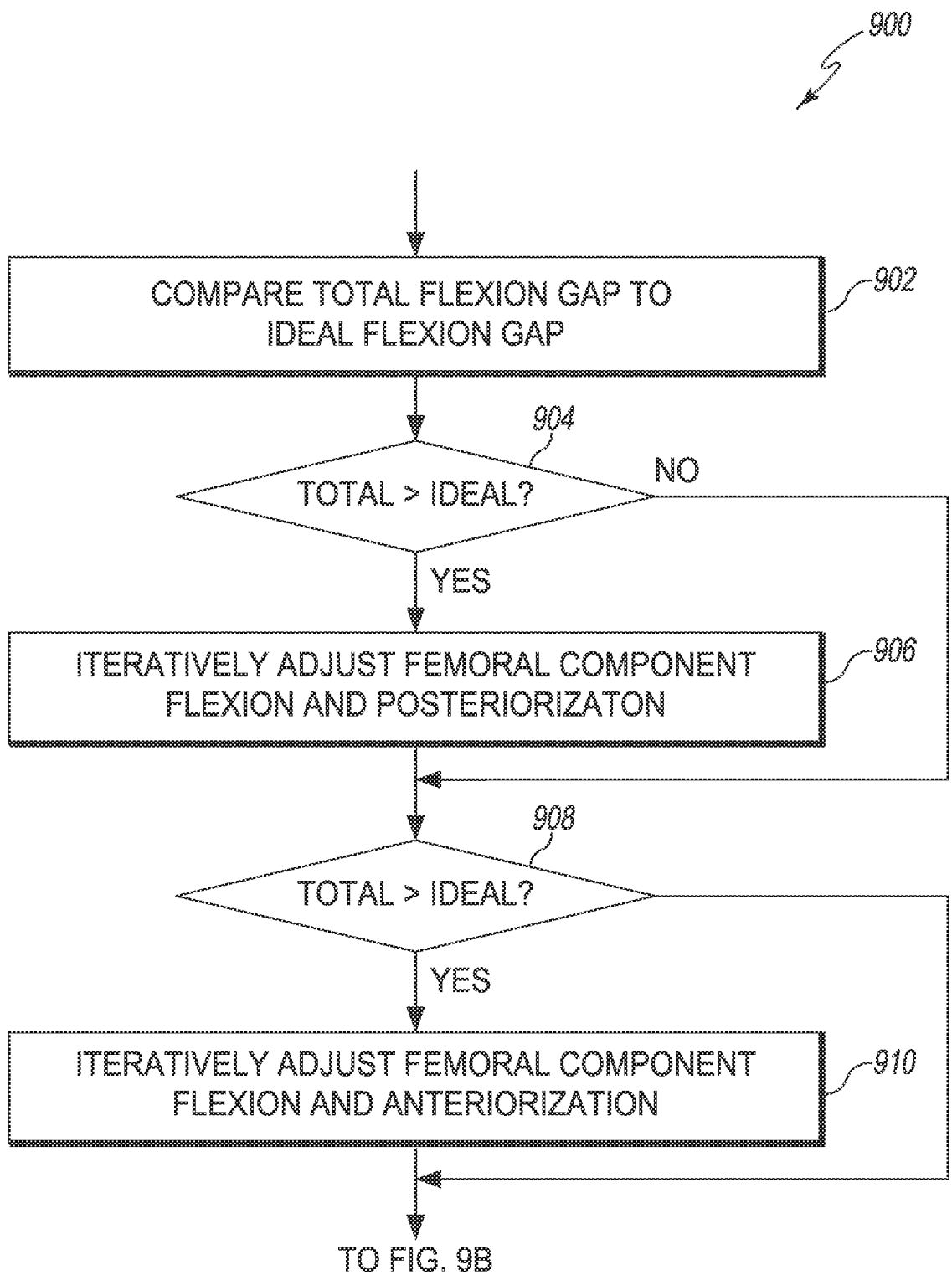
FIGS. 9A and 9B are a simplified flow diagram of a method for automatically adjusting femoral flexion that may be performed by the surgical planning and assistance device of FIGS. 1-2.
Figure 9B:
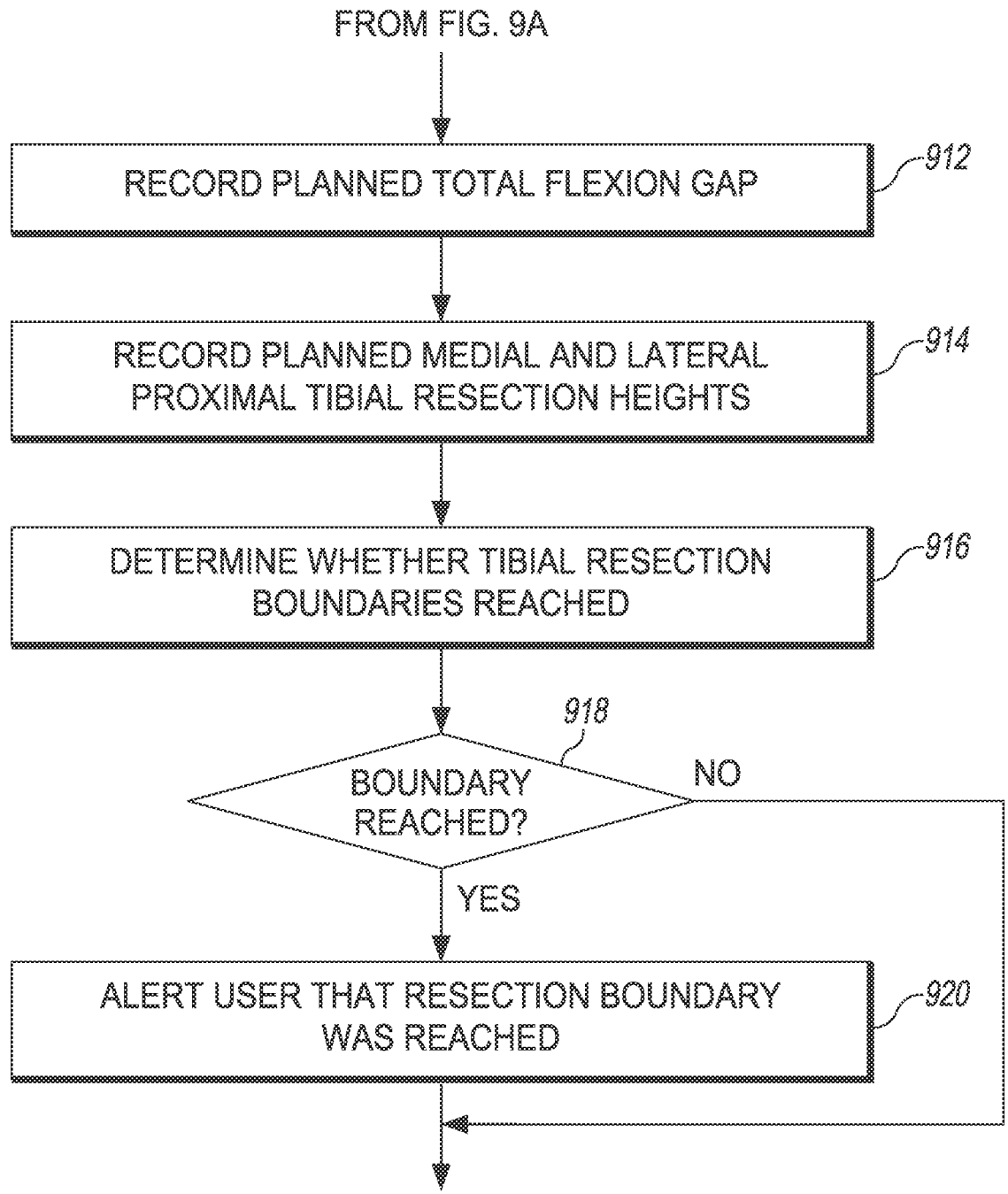
Figure 10A:
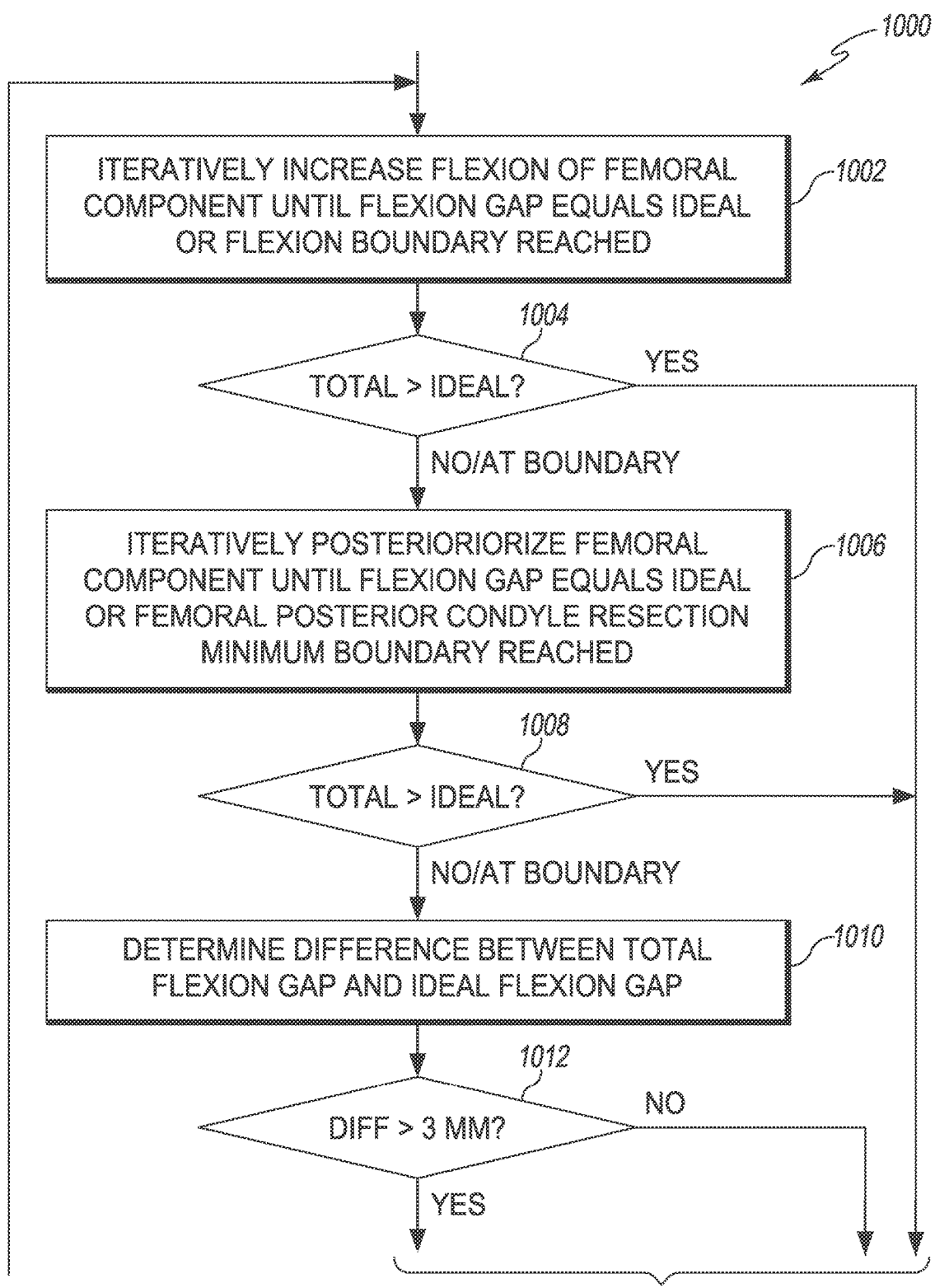
Figure 11A:
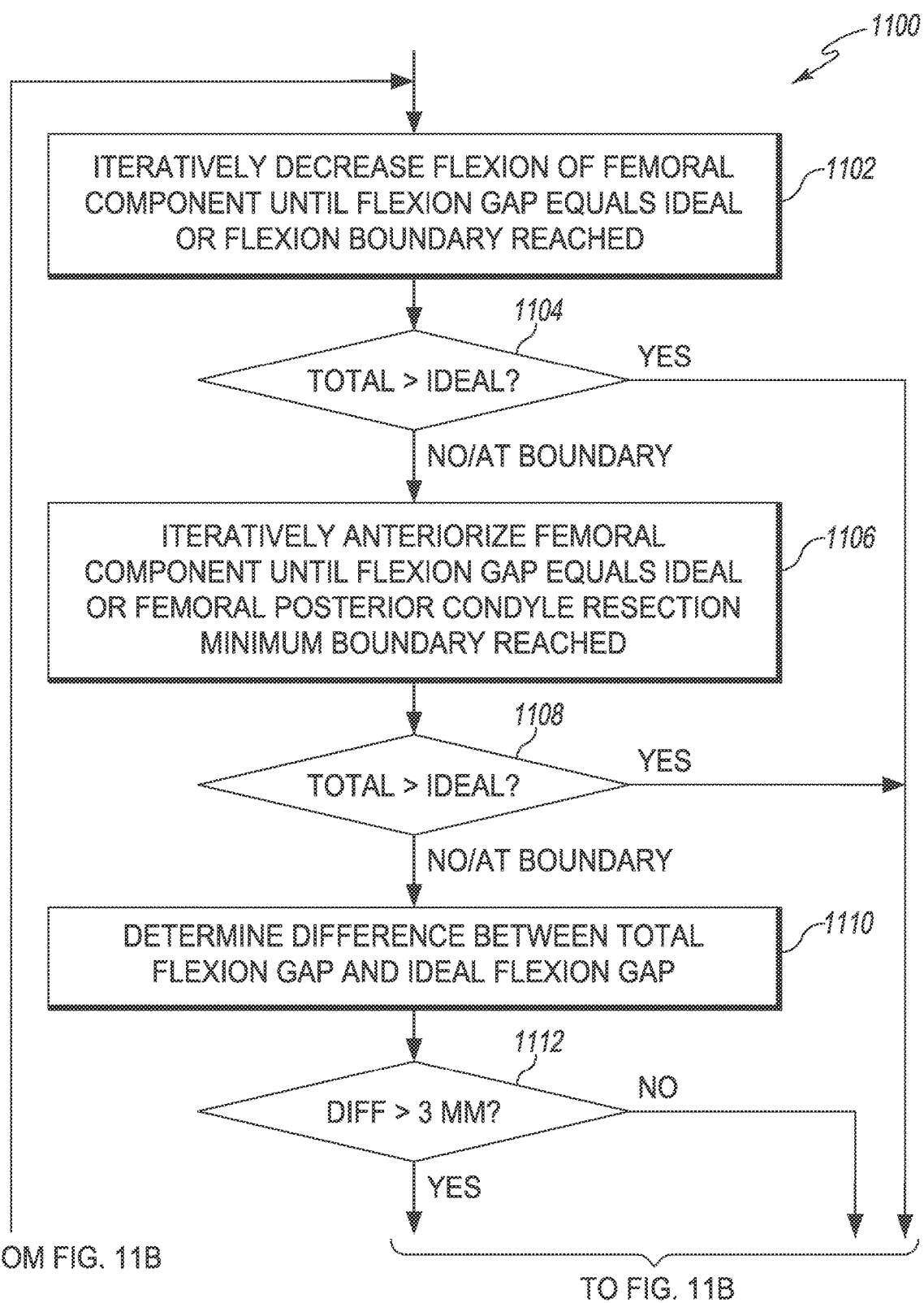
FIGS. 11A and 11B are a simplified flow diagram of a method for automatically adjusting femoral flexion and anteriorization that may be performed by the surgical planning and assistance device of FIGS. 1-2.
Figure 11B:
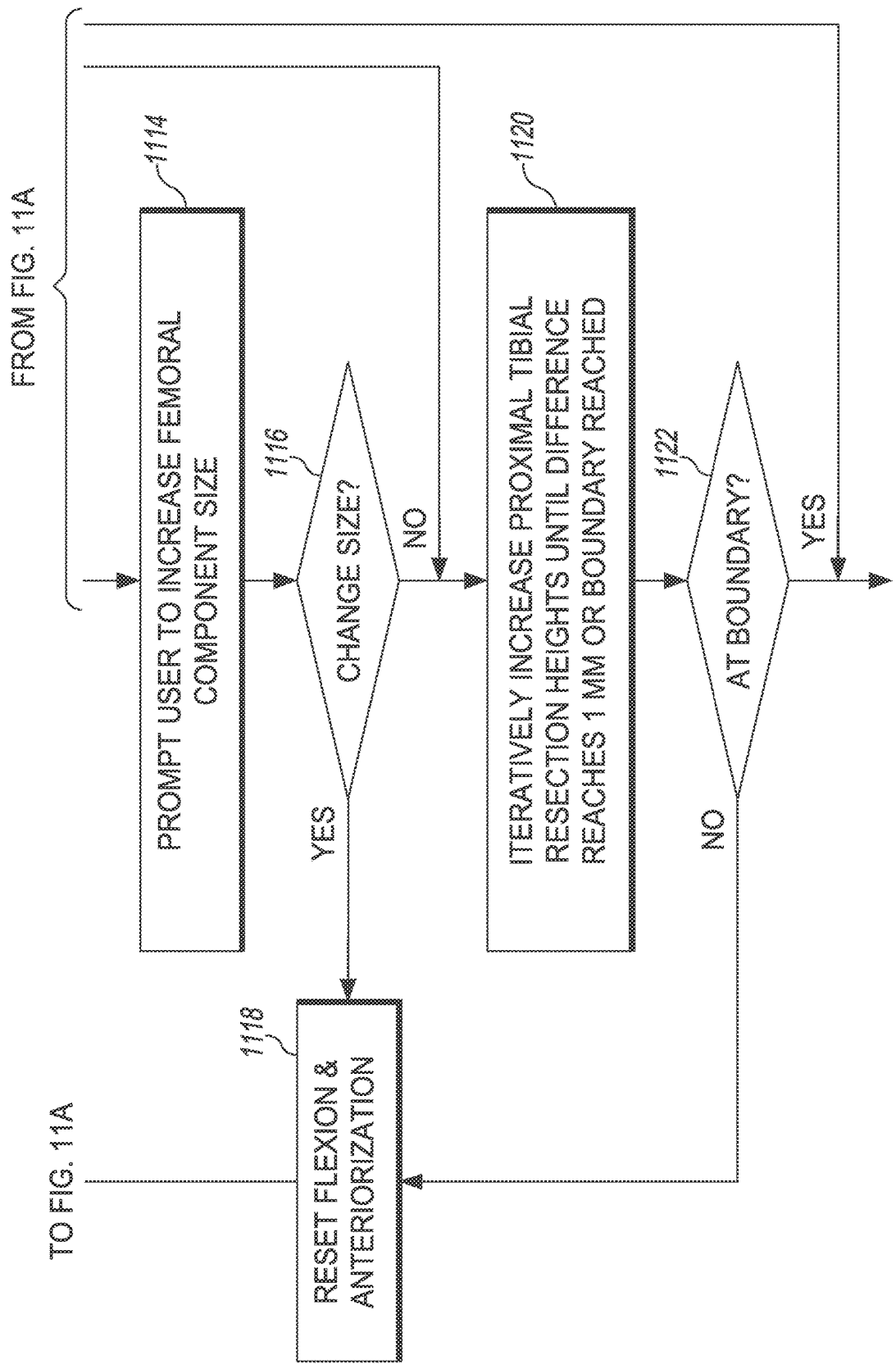

After adjusting tibial and femoral coronal alignment, the device 102 automatically adjusts femoral flexion in block 606. To adjust the femoral flexion, the device 102 iteratively adjusts the femoral component flexion/extension angle and anterior/posterior shift while remaining within boundaries for the flexion gap and for posterior femoral condyle resection height from the surgeon preferences 210. In some circumstances, the device 102 may also iteratively adjust the proximal tibia resection heights that were previously determined as described above in connection with block 602 while also remaining within boundaries for proximal tibia resection height from the surgeon preferences 210. The particular strategy used for adjusting femoral flexion and anterior/posterior shift may depend on whether the flexion gap is initially greater than ideal (i.e., too loose) or less than ideal (i.e., too tight). Potential embodiments for methods for automatically adjusting femoral flexion are shown in FIGS. 9-11 and described below (see also graphical representation 1418 in FIG. 14).

Figure 12:
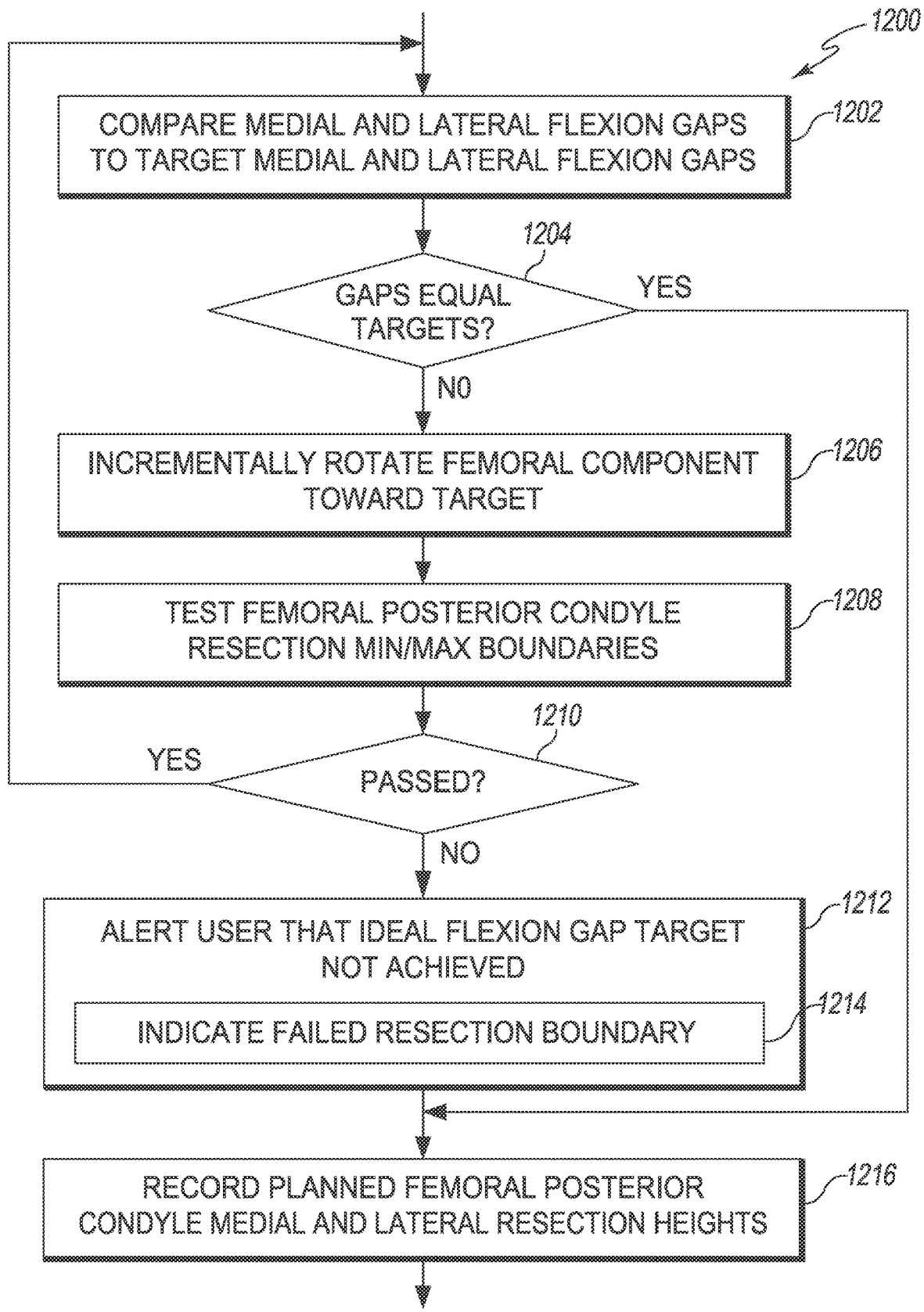
FIG. 12 is a simplified flow diagram of a method for automatically adjusting femoral rotation that may be performed by the surgical planning and assistance device of FIGS. 1-2.

In block 608, the device 102 automatically adjusts femoral rotation. The device 102 may iteratively adjust femoral rotation, which may cause corresponding changes to posterior femoral condyle resection height. Accordingly, the device 102 may adjust femoral rotation while remaining within boundaries for posterior femoral condyle resection height from the surgeon preferences 210. One potential embodiment for automatically adjusting femoral rotation is shown in FIG. 12 and described below (see also graphical representation 1410 in FIG. 14).

Figure 13:
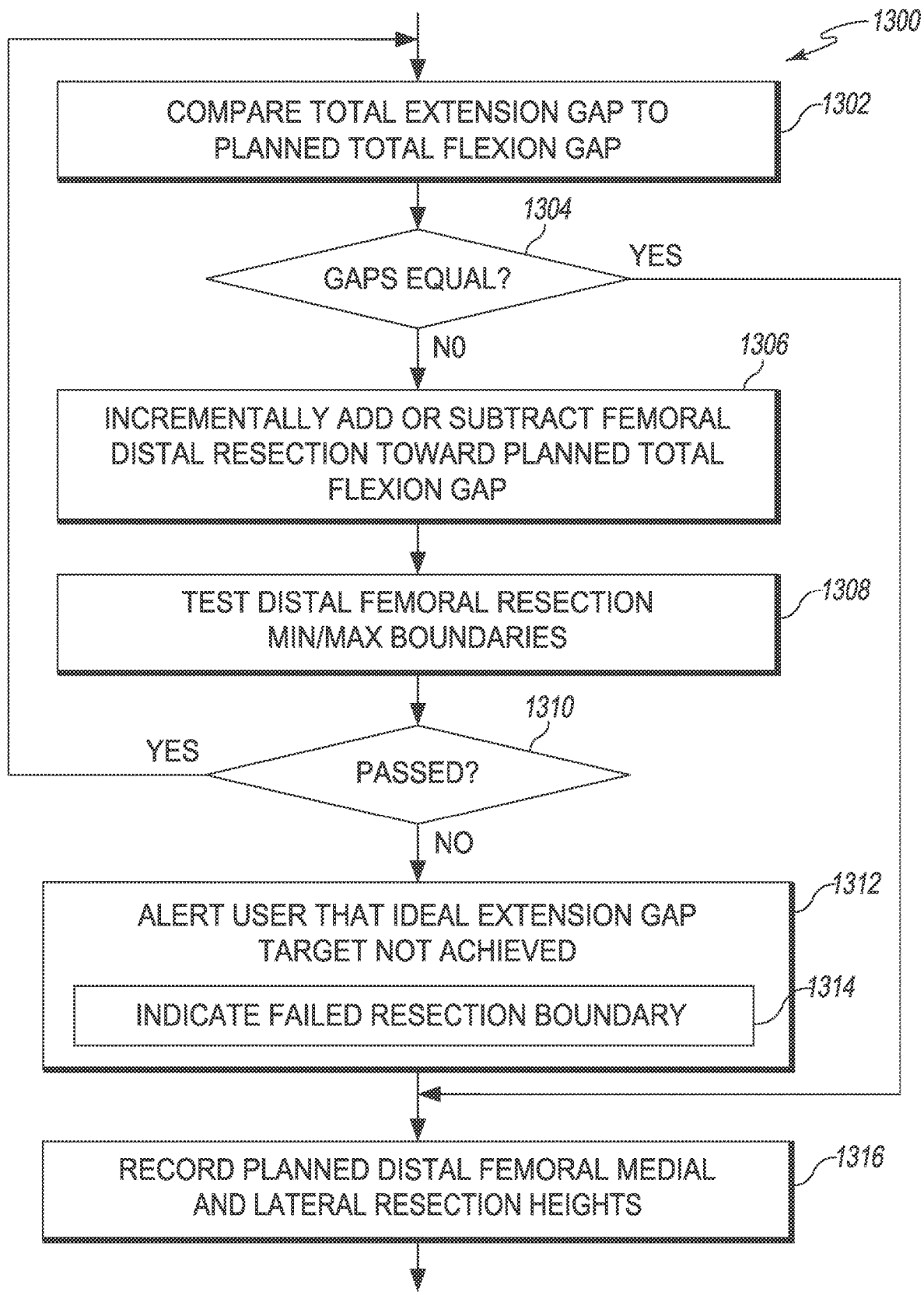
FIG. 13 is a simplified flow diagram of a method for automatically adjusting medial and lateral distal femoral condyle resection heights that may be performed by the surgical planning and assistance device of FIGS. 1-2.

In block 610, the device 102 automatically adjusts the medial and lateral distal femoral condyle resection heights while remaining within boundaries for the distal femoral condyle resection heights from the surgeon preferences 210. Note that adjusting the distal femoral condyle resection heights also affects the extension gap. One potential embodiment for automatically adjusting distal femoral condyle resection heights is shown in FIG. 13 and described below (see also graphical representation 1410 in FIG. 14). After adjusting distal femoral condyle resection heights, the method 600, and thus the surgical plan 212, is completed. The device 102 may continue with presenting the determined surgical plan 212 as described above in connection with the method 300 of FIG. 3.

Referring now to FIG. 7, in use, the device 102 may perform a method 700 for automatically adjusting tibial coronal alignment. It should be appreciated that in some embodiments, the operations of the method 700 may be performed in connection with block 602 of FIG. 6, described above. The method 700 begins with block 702, in which the device 102 determines the tibial high side based on the bony registration. The device 102 may identify either the medial tibial plateau or the lateral tibial plateau as the high side based on which side has the most-proximal point according to the bony registration. In block 704, the device 102 determines whether the high side is the lateral side. If so, the method 700 branches to block 708. If the high side is not the lateral side, the method 700 advances to block 706, in which the device 102 prompts the user to verify the tibial registration.

In block 708, the device 102 determines initial medial and lateral proximal tibia resection heights based on target values from the surgeon preferences 210 and the estimated cartilage loss. For example, the initial medial proximal tibia resection height may be the target medial resection height minus the estimated medial tibial cartilage loss, and the initial lateral proximal tibia resection height may be the target lateral resection height minus the estimated lateral tibial cartilage loss.

In block 710, the device 102 determines the tibial *varus/valgus* joint line angle based on the medial and lateral proximal tibia resection heights. In block 712, the device 102 tests the *varus/valgus* joint line angle against the tibial *varus/valgus* boundaries of the surgeon preferences 210. In particular, the device 102 may determine whether the angle is between the maximum *valgus* boundary and the maximum *varus* boundary. In block 714, the device 102 determines whether the tibial *varus/valgus* joint line angle is within the boundaries. If so, the method 700 branches ahead to block 722, described below. If the tibial *varus/valgus* joint line angle is not within the boundaries, the method 700 advances to block 716. In some embodiments, the presence of patellofemoral instability can be accounted for by limiting the degree of rotation and, by extension, tibial *varus*. This function could be provided, for example, in response to a toggle switch or other user interface control that may be activated before or after the surgical plan 212 is created.

In block 716, the device 102 incrementally decreases the low-side proximal tibia resection height. The device 102 may decrease the low-side resection height by a small amount, such as 0.5 mm. For example, if the lateral side is the high side, the device 102 may reduce the medial proximal tibia resection height by 0.5 mm. In block 718, the device 102 tests the low-side resection height against the minimum proximal tibia resection height boundary of the surgeon preferences 210, for example by determining whether the low-side resection height is greater than or equal to the minimum boundary. In block 720, the device 102 determines whether the low-side proximal tibia resection height is within boundaries. If so, the method 700 loops back to block 710, in which the device 102 continues to incrementally adjust the resection height. If the low-side proximal tibia resection height is not within bounds (e.g., less than and/or less than or equal to the minimum boundary), the method 700 advances to block 722.

In block 722, the device 102 records a temporary or provisional medial proximal tibia resection height and lateral proximal tibia resection height. As described further below, those temporary or provisional values may be further adjusted while determining other parameters of the surgical plan 212. After recording the medial and lateral proximal tibia resection heights, the method 700 is completed. The device 102 may continue automatically determining the surgical plan 212 as described above in connection with FIG. 6.

Referring now to FIG. 8, in use, the device 102 may perform a method 800 for automatically adjusting femoral coronal alignment. It should be appreciated that in some embodiments, the operations of the method 800 may be performed in connection with block 604 of FIG. 6, described above. The method 800 begins with block 802, in which the device 102 determines initial values for medial distal femoral condyle resection height and lateral distal femoral condyle resection height based on the target value from the surgeon preferences 210 and the estimated cartilage loss. For example, the medial distal femoral condyle resection height may equal the target medial distal femoral condyle resection height minus the estimated medial distal femoral condyle cartilage loss, and the lateral distal femoral condyle resection height may equal the target lateral distal femoral condyle resection height minus the estimated lateral distal femoral condyle cartilage loss. In block 804, the device 102 determines the pivot point as the opposite side of the joint from the side having the smallest extension gap. For example, if the medial extension gap is smaller than the lateral extension gap, the pivot point is on the lateral side, and if the medial extension gap is larger than the lateral extension gap, the pivot point is on the medial side.

In block 806, the device 102 determines whether the medial and lateral extension gaps are equal. Initial values for the medial and lateral extension gaps are determined during leg-alignment registration as described above. Calculated values of the medial and lateral extension gaps may be determined in response to adjustments to the distal femoral condyle extension gap. In block 808, the device 102 checks whether the medial and lateral extension gaps are equal. If so, the method 800 branches to block 822, described below. If not, the method 800 advances to block 810.

In block 810, the device 102 incrementally increases the distal femoral condyle resection height of the side of the joint with the smallest extension gap. The device 102 may incrementally increase the resection height by a small amount, such as 0.5 mm. For example, if the medial side has the smallest gap, the device 102 may increase the medial distal femoral condyle resection height by 0.5 mm, and if the lateral side has the smallest gap, the device 102 may increase the lateral distal femoral condyle resection height by 0.5 mm.

In block 812, the device 102 determines a femoral *varus/valgus* angle based on the medial and lateral distal femoral condyle resection heights. In block 814, the device 102 the device 102 tests the *varus/valgus* angle against the femoral *varus/valgus* boundaries of the surgeon preferences 210. In particular, the device 102 may determine whether the angle is between the maximum *valgus* boundary and the maximum *varus* boundary. In block 816, the device 102 determines whether the femoral *varus/valgus* joint line angle is within the boundaries. If not, the method 800 branches ahead to block 822, described below. If the femoral *varus/valgus* joint line angle is within the boundaries, the method 800 advances to block 818, in which the device 102 tests the medial and lateral distal femoral condyle resection heights against the maximum medial and lateral distal femoral condyle resection height boundaries of the surgeon preferences 210, for example by determining whether each distal femoral condyle resection height is less than or equal to the maximum boundary. In block 820, the device 102 determines whether the medial and lateral distal femoral condyle resection heights are within boundaries. If so, the method 800 loops back to block 806, in which the device 102 continues to incrementally adjust the resection height until the medial and lateral extension gaps are equal. If the medial and lateral distal femoral condyle resection heights are not within bounds (e.g., greater than and/or greater than or equal to the maximum boundary), the method 800 advances to block 822.

In block 822, the device 102 records a temporary or provisional medial distal femoral condyle resection height and lateral distal femoral condyle resection height. As described further below, those temporary or provisional values may be further adjusted while determining other parameters of the surgical plan 212. After recording the medial and lateral distal femoral condyle resection heights, the method 800 is completed. The device 102 may continue automatically determining the surgical plan 212 as described above in connection with FIG. 6.

Referring now to FIG. 9, in use, the device 102 may perform a method 900 for automatically adjusting femoral flexion. It should be appreciated that in some embodiments, the operations of the method 900 may be performed in connection with block 606 of FIG. 6, described above. The method 900 begins with block 902, in which the device 102 compares the total flexion gap to the ideal flexion gap. In block 904, the device 102 checks whether the total flexion gap is greater than the ideal flexion gap. If not, the method 900 branches ahead to block 908, described below. If the total flexion gap is greater than the ideal flexion gap, the method 900 advances to block 906.

In block 906, the device 102 iteratively adjusts femoral component flexion and posteriorization in the surgical plan 212. The device 102 maintains femoral component flexion and posteriorization within boundaries of the surgeon preferences 210. When those boundaries are met, the device 102 may also adjust the medial and lateral proximal tibia resection heights and/or the implant size in use. One potential embodiment of a method for adjusting femoral flexion and posteriorization is shown in FIG. 10 and described below.

In block 908, the device 102 determines whether the total flexion gap is less than the ideal flexion gap. If not (i.e., if the total flexion gap equals the ideal flexion gap), the method 900 branches ahead to block 912, described below. If the total flexion gap is less than the ideal flexion gap, the method 900 advances to block 910.

In block 906, the device 102 iteratively adjusts femoral component flexion and anteriorization in the surgical plan 212. The device 102 maintains femoral component flexion and anteriorization within boundaries of the surgeon preferences 210. When those boundaries are met, the device 102 may also adjust the medial and lateral proximal tibia resection heights and/or the implant size in use. One potential embodiment of a method for adjusting flexion and anteriorization is shown in FIG. 11 and described below.

After appropriately adjusting the femoral component flexion and/or anterior-posterior shift, the device 102 records the planned total flexion gap in block 912. In block 914, the device 102 records the planned medial and lateral proximal tibia resection heights, for example in the surgical plan 212.

In block 916, the device 102 determines whether any tibial resection boundaries were reached. For example, the device 102 may determine whether the medial proximal tibia resection height equals the minimum or maximum medial proximal tibia resection height, and similarly may determine whether the lateral proximal tibia resection height equals the minimum or maximum lateral proximal tibia resection height. In block 918, the device 102 checks whether any boundary was reached. If not, the method 900 is completed. The device 102 may continue automatically determining the surgical plan 212 as described above in connection with FIG. 6. Referring again to block 918, if any proximal tibia resection height boundary was met, the method 900 advances to block 920, in which the device 102 alerts a user that the resection boundary was met. After alerting the user, the method 900 is completed, and the device 102 may continue automatically determining the surgical plan 212 as described above in connection with FIG. 6. If desired, the user may modify the surgical plan 212 (e.g., to adjust the particular boundary that was met) as described above in connection with FIG. 3.

Referring now to FIG. 10, in use, the device 102 may perform a method 1000 for automatically adjusting femoral component flexion and posteriorization. It should be appreciated that in some embodiments, the operations of the method 1000 may be performed in connection with block 906 of FIG. 9, described above. The method 1000 begins with block 1002, in which the device 102 iteratively increases the flexion angle of the femoral component in the surgical plan 212 until the total flexion gap equals the ideal flexion gap or until the flexion boundary of the surgeon preferences 210 is reached. For example, the device 102 may increase the flexion angle by a small amount (e.g., 0.5 degrees, 1 degree, or other small amount) and then update other affected parameters of the surgical plan 212 including the medial and lateral posterior femoral condyle resection heights. Based on the updated surgical plan 212, the device 102 may update the total flexion gap, which equals the lateral flexion gap plus the medial flexion gap. The device 102 may test the flexion gap and the surgeon preference boundaries after incrementing the femoral flexion, for each iteration.

In block 1004, the device 102 checks whether the total flexion gap equals the ideal flexion gap. If so, the method 1000 is completed. The device 102 may continue automatically adjusting the flexion gap as described above in connection with FIG. 9. Referring again to block 1004, if the total flexion gap does not equal the ideal flexion gap (i.e., the flexion boundary and/or minimum posterior femoral condyle resection height boundary has been reached), the method 1000 advances to block 1006.

In block 1006, the device 102 iteratively posteriorizes the femoral component in the surgical plan 212 until the total flexion gap equals the ideal flexion gap or until a posterior femoral condyle resection height minimum boundary of the surgeon preferences 210 is reached. For example, the device 102 may move the femoral component a small amount in the posterior direction (e.g., 0.5 mm) and then update other affected parameters of the surgical plan 212 including the medial and lateral posterior femoral condyle resection heights. Based on the updated surgical plan 212, the device 102 may update the total flexion gap. The device 102 may test the flexion gap and the surgeon preference boundaries after incrementing the femoral component posteriorization, for each iteration.

In block 1008, the device 102 checks whether the total flexion gap equals the ideal flexion gap. If so, the method 1000 is completed. The device 102 may continue automatically adjusting the femoral flexion as described above in connection with FIG. 9. Referring again to block 1008, if the total flexion gap does not equal the ideal flexion gap (i.e., the minimum posterior femoral condyle resection height boundary has been reached), the method 1000 advances to block 1010.

In block 1010, the device 102 determines the difference between the current total flexion gap and the ideal flexion gap. If that difference is not more than 3 millimeters, the method 1000 branches to block 1020, described below. If the difference is greater than 3 millimeters, the method 1000 advances to block 1016. Although illustrated as testing the difference against 3 millimeters, it should be understood that in other embodiments, the difference may be tested against a different predetermined length. For example, the difference may be tested against the difference in anterior-posterior length between different available sizes of femoral component (which, in the illustrative embodiment, is 3 mm).

In block 1014, the device 102 prompts the user to increase the femoral component size. As described above, in the illustrative embodiment, femoral components are available in multiple predetermined sizes, and the sizes differ from each other by 3-millimeter increments in the anterior-posterior dimension. Accordingly, if the difference between the current total flexion gap and the ideal flexion gap is greater than 3 millimeters, the surgeon may consider increasing the size of the femoral component in order to reduce the flexion gap. In response to the prompt, the surgeon or other user may instruct the device 102 to increase the femoral component size, for example using the touchscreen display 130. In block 1016, the device 102 checks whether the surgeon or other user requested to change the component size. If not, the method 1000 advances to block 1020, described below. If the user elects to increase the femoral component size, the method 1000 branches to block 1018, in which the device 102 increases the femoral component size accordingly and then resets femoral component flexion and posteriorization to default values. After resetting femoral component flexion and posteriorization, the method 1000 loops back to block 1002 to continue automatically adjusting femoral flexion and posteriorization.

Referring back to blocks 1012, 1016, if the difference in size is not greater than 3 millimeters or the user does not increase the femoral component size, the method 1000 advances to block 1020. In block 1020, the device 102 iteratively reduces the proximal tibia resection heights of the surgical plan 212 until the difference between the total flexion gap and the ideal flexion gap reaches 3 millimeters, or until the proximal tibia resection height minimum boundary of the surgeon preferences 210 is reached. For example, the device 102 may reduce the medial and lateral proximal tibia resection height by a small amount (e.g., 0.5 mm) and then update the total flexion gap. The device 102 may test the flexion gap and the surgeon preference boundaries after decrementing the proximal tibia resection height, for each iteration.

In block 1022, the device 102 determines whether the proximal tibia resection height reached the minimum boundary. If not, the method 1022 branches to block 1018, in which the device 102 resets femoral component flexion and posteriorization and continues automatically adjusting flexion and posteriorization as described above. Referring back to block 1022, if the proximal tibia resection height minimum boundary is reached, the method 1000 is completed. The device 102 may continue automatically adjusting the femoral flexion as described above in connection with FIG. 9, and the device 102 may continue automatically determining the surgical plan 212 as described above in connection with FIG. 6. As described above, the device 102 may indicate to the surgeon that the boundary was met, and the surgeon may update the surgeon preferences 210.

Referring now to FIG. 11, in use, the device 102 may perform a method 1100 for automatically adjusting femoral component flexion and anteriorization. It should be appreciated that in some embodiments, the operations of the method 1100 may be performed in connection with block 910 of FIG. 9, described above. The method 1100 begins with block 1102, in which the device 102 iteratively decreases the flexion angle of the femoral component in the surgical plan 212 until the total flexion gap equals the ideal flexion gap or until the extension boundary of the surgeon preferences 210 is reached. For example, the device 102 may decrease the flexion angle by a small amount (e.g., 0.5 degrees, 1 degree, or other small amount) and then update other affected parameters of the surgical plan 212 including the medial and lateral posterior femoral condyle resection heights. Based on the updated surgical plan 212, the device 102 may update the total flexion gap, which equals the lateral flexion gap plus the medial flexion gap. The device 102 may test the flexion gap and the surgeon preference boundaries after decrementing the femoral flexion, for each iteration.

In block 1104, the device 102 checks whether the total flexion gap equals the ideal flexion gap. If so, the method 1100 is completed. The device 102 may continue automatically adjusting the femoral flexion as described above in connection with FIG. 9. Referring again to block 1104, if the total flexion gap does not equal the ideal flexion gap (i.e., the extension boundary and/or maximum posterior femoral condyle resection height boundary has been reached), the method 1100 advances to block 1106.

In block 1106, the device 102 iteratively anteriorizes the femoral component in the surgical plan 212 until the total flexion gap equals the ideal flexion gap or until a posterior femoral condyle resection height maximum boundary of the surgeon preferences 210 is reached. For example, the device 102 may move the femoral component a small amount in the anterior direction (e.g., 0.5 mm) and then update other affected parameters of the surgical plan 212 including the medial and lateral posterior femoral condyle resection heights. Based on the updated surgical plan 212, the device 102 may update the total flexion gap. The device 102 may test the flexion gap and the surgeon preference boundaries after incrementing the femoral component anteriorization, for each iteration.

In block 1108, the device 102 checks whether the total flexion gap equals the ideal flexion gap. If so, the method 1100 is completed. The device 102 may continue automatically adjusting the femoral flexion as described above in connection with FIG. 9. Referring again to block 1108, if the total flexion gap does not equal the ideal flexion gap (i.e., the maximum posterior femoral condyle resection height boundary has been reached), the method 1100 advances to block 1110.

In block 1110, the device 102 determines the difference between the current total flexion gap and the ideal flexion gap. If that difference is not more than 3 millimeters, the method 1100 branches to block 1120, described below. If the difference is greater than 3 millimeters, the method 1100 advances to block 1116. Although illustrated as testing the difference against 3 millimeters, it should be understood that in other embodiments, the difference may be tested against a different predetermined length. For example, the difference may be tested against the difference in anterior-posterior length between different available sizes of femoral component (which, in the illustrative embodiment, is 3 mm).

In block 1114, the device 102 prompts the user to decrease the femoral component size. As described above, in the illustrative embodiment, femoral components are available in multiple predetermined sizes, and the sizes differ from each other by 3-millimeter increments in the anterior-posterior dimension. Accordingly, if the difference between the current total flexion gap and the ideal flexion gap is greater than 3 millimeters, the surgeon may consider decreasing the size of the femoral component in order to increase the flexion gap. In response to the prompt, the surgeon or other user may instruct the device 102 to decrease the femoral component size, for example using the touchscreen display 130. In block 1116, the device 102 checks whether the surgeon or other user requested to change the component size. If not, the method 1100 advances to block 1120, described below. If the user elects to decrease the femoral component size, the method 1100 branches to block 1118, in which the device 102 decreases the femoral component size accordingly and then resets femoral component flexion and anteriorization to default values. After resetting femoral component flexion and anteriorization, the method 1100 loops back to block 1102 to continue automatically adjusting femoral flexion and anteriorization.

Referring back to blocks 1112, 1116, if the difference in size is not greater than 3 millimeters or the user does not decrease the femoral component size, the method 1100 advances to block 1120. In block 1120, the device 102 iteratively increases the proximal tibia resection heights of the surgical plan 212 until the difference between the total flexion gap and the ideal flexion gap reaches 1 millimeter, or until the proximal tibia resection height maximum boundary of the surgeon preferences 210 is reached. For example, the device 102 may increase the medial and lateral proximal tibia resection height by a small amount (e.g., 0.5 mm) and then update the total flexion gap. The device 102 may test the flexion gap and the surgeon preference boundaries after incrementing the proximal tibia resection height, for each iteration.

In block 1122, the device 102 determines whether the proximal tibia resection height reached the maximum boundary. If not, the method 1122 branches to block 1118, in which the device 102 resets femoral component flexion and anteriorization and continues automatically adjusting femoral flexion and anteriorization as described above. Referring back to block 1122, if the proximal tibia resection height maximum boundary is reached, the method 1100 is completed. The device 102 may continue automatically adjusting the femoral flexion as described above in connection with FIG. 9, and the device 102 may continue automatically determining the surgical plan 212 as described above in connection with FIG. 6. As described above, the device 102 may indicate to the surgeon that the boundary was met, and the surgeon may update the surgeon preferences 210.

Referring now to FIG. 12, in use, the device 102 may perform a method 1200 for automatically adjusting femoral rotation. It should be appreciated that in some embodiments, the operations of the method 1200 may be performed in connection with block 608 of FIG. 6, described above. The method 1200 begins with block 1202, in which the device 102 compares the current medial and lateral flexion gaps to the target medial and lateral flexion gaps from the surgeon preferences 210. The device 102 may determine the current medial and lateral flexion gaps based on the leg-alignment registration and the current surgical parameters of the surgical plan 212. In block 1204, the device 102 determines whether each of the medial and lateral flexion gaps equals the corresponding medial and lateral target flexion gap. If so, the method 1200 advances to block 1216, described below. If the flexion gaps do not equal the target values, the method 1200 advances to block 1206.

In block 1206, the device 102 incrementally rotates the femoral component in the surgical plan 212 toward the target values. For example, the device 102 may adjust the femoral component rotation angle by a small amount (e.g., 0.5 degrees, 1 degree, or other small amount) in a direction that will make the medial and lateral flexion gaps closer to their target values. For example, if the medial flexion gap is larger than the target medial flexion gap, the femoral component may be rotated toward the medial side to reduce the medial flexion gap. As another example, if the medial flexion gap is smaller than the target medial flexion gap, the femoral component may be rotated away from the medial side to increase the medial flexion gap. After adjusting the femoral rotation, the device 102 updates the other affected parameters of the surgical plan 212, including the medial and lateral posterior femoral condyle resection heights. In block 1208, the device 102 tests the updated medial and lateral posterior femoral condyle resection heights against the minimum and maximum posterior femoral condyle resection height boundaries of the surgeon preferences 210. In block 1210, the device 102 checks whether the medial and lateral posterior femoral condyle resection heights are within the minimum and maximum boundaries. If so, the method 1200 loops back to block 1202 to continue adjusting femoral component rotation. If not, the method 1200 advances to block 1212.

In block 1212, the device 102 alerts the surgeon or other user that the ideal flexion gap targets were not achieved. The device 102 may display the alert on the display 130 or otherwise alert the user. In block 1214, the device 102 indicates the failed resection boundary, for example the medial or lateral posterior femoral condyle resection height minimum boundary or the medial or lateral posterior femoral condyle resection height maximum boundary. In some embodiments, the surgeon may adjust the failed boundary and regenerate the surgical plan 212 as described above.

After equalizing the medial and lateral flexion gaps or after reaching a resection boundary, the device 102 records the planned medial and lateral posterior femoral condyle resection heights in the surgical plan 212 in block 1216. After recording those resection heights, the method 1200 is completed, and the device 102 may continue automatically determining the surgical plan 212 as described above in connection with FIG. 6. If desired, the user may modify the surgical plan 212 (e.g., to adjust the particular boundary that was met) as described above in connection with FIG. 3.

Referring now to FIG. 13, in use, the device 102 may perform a method 1300 for automatically adjusting medial and lateral distal femoral condyle resection heights. It should be appreciated that in some embodiments, the operations of the method 1300 may be performed in connection with block 610 of FIG. 6, described above. The method 1300 begins with block 1302, in which the device 102 compares the current total extension gap to the planned total flexion gap determined as described above in connection with FIG. 12. The device 102 may determine the current total extension gap based on the leg-alignment registration and the current surgical parameters of the surgical plan 212. In block 1304, the device 102 determines whether the total extension gap equals the total flexion gap. If so, the method 1300 advances to block 1316, described below. If the flexion and extension gaps are not equal, the method 1300 advances to block 1306.

In block 1306, the device 102 incrementally adds or subtracts from the distal femoral condyle resection heights in the surgical plan 212 to adjust the extension gap toward the planned flexion gap. For example, the device 102 may adjust both the medial and lateral distal femoral condyle resection heights by a small amount (e.g., 0.5 mm other small amount) in a direction that will make the total extension gap closer to the flexion gap. For example, if the total extension gap is larger than the total flexion gap, the distal femoral condyle resection heights may be reduced to reduce the total extension gap. As another example, if the total extension gap is smaller than the total flexion gap, the distal femoral condyle resection heights may be increased to increase the medial flexion gap. In block 1308, the device 102 tests the updated medial and lateral distal femoral condyle resection heights against the minimum and maximum distal femoral condyle resection height boundaries of the surgeon preferences 210. In block 1310, the device 102 checks whether the medial and lateral distal femoral condyle resection heights are within the minimum and maximum boundaries. If so, the method 1300 loops back to block 1302 to continue adjusting the extension gap. If not, the method 1300 advances to block 1312.

In block 1312, the device 102 alerts the surgeon or other user that the ideal extension gap target was not achieved. The device 102 may display the alert on the display 130 or otherwise alert the user. In block 1314, the device 102 indicates the failed resection boundary, for example the medial or lateral distal femoral condyle resection height minimum boundary or the medial or lateral distal femoral condyle resection height maximum boundary. In some embodiments, the surgeon may adjust the failed boundary and regenerate the surgical plan 212 as described above.

After equalizing the extension and flexion gaps or after reaching a resection boundary, the device 102 records the planned medial and lateral distal femoral condyle resection heights in the surgical plan 212 in block 1316. After recording those resection heights, the method 1300 is completed, and the device 102 may continue automatically determining the surgical plan 212 as described above in connection with FIG. 6. If desired, the user may modify the surgical plan 212 (e.g., to adjust the particular boundary that was met) as described above in connection with FIG. 3. In some embodiments, the surgical plan 212 may be presented to a user, and the user may modify the surgical plan 212, using a graphical user interface, as described below.

Referring now to FIG. 14, an illustrative embodiment of a graphical user interface 1400 that may be provided by the device 102 using the touchscreen display 130 is shown. The device 102 may provide the user interface 1400, for example, to allow a surgeon or other user to view and/or modify the surgeon preferences 210. Accordingly, the user interface 1400 includes multiple user interface controls that allow the surgeon or other user to view and edit values of the surgeon preferences 210. As shown in FIG. 14, the user interface 1400 also includes graphical representations of the current surgical plan 212 in relation to the patient's anatomy.

The user interface 1400 includes a graphical representation 1402 of an anterior view of the femoral component superimposed on the femur in extension, which illustrates femoral coronal alignment. This portion of the user interface 1400 also includes controls 1404, 1406 for the medial and lateral distal femoral condyle resection heights, respectively. The user may input target values for the distal femoral condyle resection heights by tapping on or otherwise activating the associated user controls 1404, 1406. Additionally, in some embodiments the user may input boundary values (e.g., maximum and minimum resection heights) with the user controls 1404, 1406, for example by activating one or more pop-up windows or other user interface controls. When the user edits one or more of the distal femoral condyle resection heights, a corresponding line shown in the graphical representation 1402 may be updated accordingly. Similarly, the user interface 1400 also includes a control 1408, which may be used to edit boundary values (e.g., minimum and maximum angles) for the femoral *varus/valgus* range. Additionally, the contents of the control 1408 and/or the dashed line in the representation 1402 may be updated to show femoral *varus/valgus* angle based on the target values of the femoral distal condyle resection heights.

The user interface 1400 further includes a graphical representation 1410 of the femoral component superimposed on the femur in flexion, which illustrates femoral rotation. This portion of the user interface 1400 also includes controls 1412, 1414 for the medial and lateral posterior femoral condyle resection heights, respectively. The user may input target values for the posterior femoral condyle resection heights by tapping on or otherwise activating the associated user controls 1412, 1414. Additionally, in some embodiments the user may input boundary values (e.g., maximum and minimum resection heights) with the user controls 1412, 1414, for example by activating one or more pop-up windows or other user interface controls. When the user edits one or more of the posterior femoral condyle resection heights, a corresponding line shown in the graphical representation 1410 may be updated accordingly. Similarly, the user interface 1400 also includes a control 1416 for femoral rotation. The control 1416 may also be used to edit boundary values for femoral rotation (e.g., minimum and maximum angles). Further, the contents of the control 1416 may be updated based on changes to the posterior femoral condyle resection heights in controls 1412, 1414, and vice versa.

The user interface 1400 also includes graphical representation 1422 of a lateral view of the femoral component superimposed on the femur in extension, which illustrates femoral flexion as well as anterior/posterior shift. This portion of the user interface 1400 includes a control 1420 that allows the user to view and/or edit femoral flexion, and may be used to edit femoral flexion boundaries (e.g., minimum and maximum values). A control 1422 allows the user to view and in some embodiments edit anterior/posterior shift (i.e., anteriorization) of the femoral component. In some embodiments, the contents of the control 1422 may be updated in response to changes in posterior femoral condyle resection heights from the controls 1412, 1414, and vice versa.

As shown, the user interface 1400 further includes a graphical representation 1424 of an anterior view of the tibia, which illustrates a tibial resection height component of tibial coronal alignment. This portion of the user interface 1400 also includes controls 1426, 1428 for the medial and lateral tibial resection heights, respectively. The user may input target values for the tibial resection heights by tapping on or otherwise activating the associated user controls 1426, 1428. Additionally, in some embodiments the user may input boundary values (e.g., maximum and minimum resection heights) with the user controls 1426, 1428, for example by activating one or more pop-up windows or other user interface controls.

The user interface 1400 includes a graphical representation 1430 of another anterior view of the tibia, which illustrates a *varus/valgus* angle component of tibial coronal alignment. A user control 1432 may be used to edit boundary values (e.g., minimum and maximum angles) for the tibial *varus/valgus* range. Additionally, the contents of the control 1432 and/or the dashed line in the representation 1430 may be updated to show tibial *varus/valgus* angle based on the target values of the tibial resection heights.

The user interface 1400 further includes a graphical representation 1434 of a lateral view of the tibial that illustrates tibial slope. A user control 1434 may be used to view and edit the target value for tibial slope, and in some embodiments may be used to edit boundary values (e.g., minimum and maximum angles) for tibial slope.

The user interface 1400 may also include additional user interface elements that provide additional information and/or allow the surgeon or other user to perform additional functions. For example, the illustrative user interface 1400 includes control group 1438 which allows the user to specify implant type and/or size. Updates to the implant type or size may be reflected in the various graphical representations 1402, 1410, 1418, 1424, 1430, 1434 of the user interface 1400. The illustrative user interface 1400 further includes a balance graph 1440, which may be updated based on values derived from the bony registration, the leg-alignment registration, and/or the surgeon preferences 210.

While certain illustrative embodiments have been described in detail in the drawings and the foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method for generating a surgical plan for an orthopaedic surgical procedure, the method comprising:
 receiving, by a computer system, a plurality of surgeon preferences comprising a target value and one or more boundary values associated with a surgical parameter of the orthopaedic surgical procedure,
 performing, with the computer system, bony registration of bony anatomy of a patient,
 performing, with the computer system, leg-alignment registration of the patient, wherein performing the leg-alignment registration comprises measuring a flexion gap of a knee joint of the patient and measuring an extension gap of the knee joint, and
 determining, by the computer system, the surgical plan for the orthopaedic surgical procedure based on the plurality of surgeon preferences, the bony registration, and the leg-alignment registration, wherein the surgical plan comprises a planned value associated with the surgical parameter of the orthopaedic surgical procedure, wherein the planned value is within the one or more boundary values associated with the surgical parameter, and wherein determining the surgical plan for the orthopaedic surgical procedure comprises automatically adjusting a tibial coronal alignment by:
  determining an initial proximal tibia resection height based on the surgeon preferences and an estimate of cartilage loss, and
  while the proximal tibia resection height is within a minimum proximal tibia resection height boundary of the surgeon preferences, iteratively decreasing the proximal tibia resection height until a coronal angle of a tibia of the patient is within a tibial *varus*/valgus boundary of the surgeon preferences.

2. The method of claim 1, further comprising:
presenting, by the computer system, the surgical plan to a user,
receiving, by the computer system, a modification of the surgical plan in response to presenting the surgical plan, wherein the modification comprises an updated boundary value associated with the surgical parameter, and
determining, by the computer system, an updated surgical plan for the orthopaedic surgical procedure based on the plurality of surgeon preferences, the bony registration, the leg-alignment registration, and the updated boundary value, wherein the updated boundary value overrides at least one of the plurality of surgeon preferences.

3. The method of claim 1, wherein determining the surgical plan for the orthopaedic surgical procedure further comprises:
  automatically adjusting a femoral coronal alignment in response to automatically adjusting the tibial coronal alignment,
  automatically adjusting a femoral flexion in response to automatically adjusting the femoral coronal alignment,
  automatically adjusting a femoral rotation in response to automatically adjusting the femoral flexion, and
  automatically adjusting a distal femoral condyle resection height in response to automatically adjusting the femoral rotation.

4. The method of claim 3, wherein automatically adjusting the femoral coronal alignment comprises:
  determining an initial distal femoral condyle resection height based on the surgeon preferences and an estimate of cartilage loss, and
  while a coronal angle of a femur of the patient is within a femoral varus/valgus boundary of the surgeon preferences, and while a distal femoral condyle resection height is within a maximum distal femoral condyle resection height boundary of the surgeon preferences, iteratively increasing the distal femoral condyle resection height until a medial extension gap equals a lateral extension gap.

5. The method of claim 3, wherein automatically adjusting the femoral flexion comprises:
  while a femoral component flexion/extension angle is within a femoral component flexion/extension boundary of the surgeon preferences, iteratively adjusting the femoral component flexion/extension angle until a total flexion gap equals an ideal flexion gap, wherein the total flexion gap comprises a sum of a lateral flexion gap and a medial flexion gap, and wherein the ideal flexion gap comprises a sum of a natural joint laxity in flexion and a predetermined component height, and
  in response to the femoral component flexion/extension angle reaching the femoral component flexion/extension boundary, while a posterior femoral condyle resection height is within a posterior femoral condyle resection height boundary of the surgeon preferences, iteratively adjusting a femoral component anterior/posterior shift until the total flexion gap equals the ideal flexion gap.

6. The method of claim 5, wherein automatically adjusting the femoral flexion further comprises:
  determining a difference between the total flexion gap and the ideal flexion gap in response to the posterior femoral condyle resection height reaching the posterior femoral condyle resection height boundary,
  determining whether the difference is greater than a predetermined length, wherein the predetermined length is associated with a femoral component size difference,
  in response to a determination that the difference is greater than the predetermined length, prompting a change to a size of the femoral component,
  in response to a determination that the difference is not greater than the predetermined length, while the proximal tibia resection height is within a proximal tibia resection height boundary, iteratively adjusting a proximal tibia resection height until the difference reaches the predetermined length, and
  in response to a changing of the size of the femoral component or iteratively adjusting of the proximal tibia resection height, resetting the femoral component flexion/extension angle and the femoral component anterior/posterior shift.

7. The method of claim 6, wherein:
when the total flexion gap is greater than the ideal flexion gap, (i) iteratively adjusting the femoral component flexion/extension angle comprises increasing the femoral component flexion angle, (ii) iteratively adjusting the femoral component anterior/posterior shift comprises increasing posteriorization of the femoral component, (iii) prompting a change to the size of the femoral component comprises prompting an increase in the size of the femoral component, and (iv) iteratively adjusting the proximal tibia resection height comprises reducing the proximal tibia resection height, and
when the total flexion gap is less than the ideal flexion gap, (i) iteratively adjusting the femoral component flexion/extension angle comprises decreasing the femoral component flexion angle, (ii) iteratively adjusting the femoral component anterior/posterior shift comprises increasing anteriorization of the femoral component, (iii) prompting a change to the size of the femoral component comprises prompting a decrease in the size of the femoral component, and (iv) iteratively adjusting the proximal tibia resection height comprises increasing the proximal tibia resection height.

8. The method of claim 3, wherein automatically adjusting the femoral rotation comprises iteratively rotating a femoral component while a posterior femoral condyle resection height is within a posterior femoral condyle resection height boundary until medial and lateral flexion gaps equal target medial and lateral flexion gaps, respectively.

9. The method of claim 3, wherein automatically adjusting the distal femoral condyle resection height comprises iteratively adjusting a distal femoral condyle resection height while the distal femoral condyle resection height is within a distal femoral condyle resection height boundary until a total extension gap equals a total flexion gap.

10. A orthopaedic surgical planning system comprising:
a computer system comprising at least one processor and at least one memory, wherein the computer system is configured to:
receive a plurality of surgeon preferences comprising a target value and one or more boundary values associated with a surgical parameter of an orthopaedic surgical procedure,
obtain registration data relating to a knee joint of a patient, wherein the registration data defines a flexion gap of the knee joint and an extension gap of the knee joint, and
determine the surgical plan for the orthopaedic surgical procedure based on the plurality of surgeon preferences and the registration data, wherein the surgical plan comprises a planned value associated with the surgical parameter of the orthopaedic surgical procedure, wherein the planned value is within the one or more boundary values associated with the surgical parameter, wherein the computer system is configured to determine the surgical plan for the orthopaedic surgical procedure by automatically adjusting the tibial coronal alignment, and wherein automatically adjusting the tibial coronal alignment comprises:
determining an initial proximal tibia resection height based on the surgeon preferences and an estimate of cartilage loss, and
while the proximal tibia resection height is within a minimum proximal tibia resection height boundary of the surgeon preferences, iteratively decreasing the proximal tibia resection height until a coronal angle of a tibia of the patient is within a tibial varus/valgus boundary of the surgeon preferences.

11. The system of claim 10, further comprising a registration tool configured to be positioned relative to a plurality of anatomical landmarks of the patient while observed by the computer system to obtain the registration data.

12. The system of claim 10, further comprising a robotic surgical device configured to position a cutting tool for resecting a bone of the patient in order to achieve the planned value of the surgical plan.

13. The system of claim 10, wherein the computer system is further configured to:
present the surgical plan to a user,
receive a modification of the surgical plan in response to presenting the surgical plan, wherein the modification comprises an updated boundary value associated with the surgical parameter, and
determine an updated surgical plan for the orthopaedic surgical procedure based on the plurality of surgeon preferences, the registration data, and the updated boundary value, wherein the updated boundary value overrides at least one of the plurality of surgeon preferences.

14. The system of claim 10, wherein the computer system is further configured to determine the surgical plan for the orthopaedic surgical procedure by:
automatically adjusting a femoral coronal alignment in response to automatically adjusting the tibial coronal alignment,
automatically adjusting a femoral flexion in response to automatically adjusting the femoral coronal alignment,
automatically adjusting a femoral rotation in response to automatically adjusting the femoral flexion, and
automatically adjusting a distal femoral condyle resection height in response to automatically adjusting the femoral rotation.

15. The system of claim 14, wherein the computer system is configured to automatically adjust the femoral coronal alignment by:
determining an initial distal femoral condyle resection height based on the surgeon preferences and an estimate of cartilage loss, and
while a coronal angle of a femur of the patient is within a femoral varus/valgus boundary of the surgeon preferences, and while a distal femoral condyle resection height is within a maximum distal femoral condyle resection height boundary of the surgeon preferences, iteratively increasing the distal femoral condyle resection height until a medial extension gap equals a lateral extension gap.

16. The system of claim 14, wherein the computer system is configured to automatically adjust the femoral flexion by:
while a femoral component flexion/extension angle is within a femoral component flexion/extension boundary of the surgeon preferences, iteratively adjusting the femoral component flexion/extension angle until a total flexion gap equals an ideal flexion gap, wherein the total flexion gap comprises a sum of a lateral flexion gap and a medial flexion gap, and wherein the ideal flexion gap comprises a sum of a natural joint laxity in flexion and a predetermined component height, and
in response to the femoral component flexion/extension angle reaching the femoral component flexion/extension boundary, while a posterior femoral condyle resection height is within a posterior femoral condyle resection height boundary of the surgeon preferences, iteratively adjusting a femoral component anterior/posterior shift until the total flexion gap equals the ideal flexion gap.

17. The system of claim 14, wherein the computer system is configured to automatically adjust the femoral rotation by iteratively rotating a femoral component while a posterior femoral condyle resection height is within a posterior femoral condyle resection height boundary until medial and lateral flexion gaps equal target medial and lateral flexion gaps, respectively.

18. The system of claim 14, wherein the computer system is configured to automatically adjust the distal femoral condyle resection height by iteratively adjusting a distal femoral condyle resection height while the distal femoral condyle resection height is within a distal femoral condyle resection height boundary until a total extension gap equals a total flexion gap.

* * * * *